US008124356B2

(12) United States Patent (10) Patent No.: US 8,124,356 B2
Sheppard et al. (45) Date of Patent: Feb. 28, 2012

(54) METHODS OF PURIFYING ZSIG33

(75) Inventors: Paul O. Sheppard, Granite Falls, WA (US); Darrell C. Conklin, London (GB)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 13/016,537

(22) Filed: Jan. 28, 2011

(65) Prior Publication Data

US 2011/0151480 A1 Jun. 23, 2011

Related U.S. Application Data

(60) Division of application No. 12/147,187, filed on Jun. 26, 2008, now Pat. No. 7,888,056, which is a continuation of application No. 09/718,803, filed on Nov. 22, 2000, now abandoned.

(60) Provisional application No. 60/166,765, filed on Nov. 22, 1999.

(51) Int. Cl.
*G01N 33/68* (2006.01)
*A61K 38/10* (2006.01)

(52) U.S. Cl. ........................................ 435/7.2; 530/325

(58) Field of Classification Search ...................... None
See application file for complete search history.

(56) References Cited

U.S. PATENT DOCUMENTS

| | | | |
|---|---|---|---|
| 3,978,035 | A | 8/1976 | Wunsch et al. |
| 5,006,469 | A | 4/1991 | Adelman et al. |
| 5,470,830 | A | 11/1995 | Macielag et al. |
| 6,291,653 | B1 | 9/2001 | Sheppard et al. |
| 6,380,158 | B1 | 4/2002 | Sheppard |
| 6,420,521 | B1 | 7/2002 | Sheppard et al. |
| 6,627,729 | B1 | 9/2003 | Sheppard et al. |
| 6,838,438 | B2 | 1/2005 | Sheppard et al. |
| 6,897,286 | B2 | 5/2005 | Jaspers et al. |
| 6,939,690 | B2 | 9/2005 | Sheppard et al. |
| 2003/0176640 | A1 | 9/2003 | Sheppard et al. |
| 2009/0081168 | A1 | 3/2009 | Sheppard et al. |

FOREIGN PATENT DOCUMENTS

| | | |
|---|---|---|
| EP | 1197496 | 4/2002 |
| WO | 97/21730 | 6/1997 |
| WO | 98/42840 | 10/1998 |
| WO | 01/07475 | 2/2001 |

OTHER PUBLICATIONS

PCT Search Report for WO 01/38355; Nov. 22, 2001.
Pearson et. al., "Molecular Biology of the Peptide Hormone Families," *Gastrointestinal Hormones in Medicine* 22(4): 753-774, 1993.
Bednarek et. al., "Structure-Function Studies on the New Growth Hormone-Releasing Peptide, Ghrelin: Minimal Sequence of Ghrelin Necessary for Activation of Growth Hormone Secretagogue Receptor 1a," *J. Med. Chem.* 43: 4370-4376, Oct. 26, 2000.
Kojima et. al., "Ghrelin is a growth-hormone-releasing acylated peptide from stomach," *Nature* 402: 656-660, Dec. 12, 1999.
Feighner et. al., "Receptor for Motilin Identified in the Human Gastrointestinal System," *Science* 284(5423): 2184-2188, Jun. 25, 1999.
Daikh et al., "Structure and Expression of the Human Motilin Gene," *DNA* 8(8): 615-621, 1989.
INC2207941, LIFESEQ™ Clone Information Results, Incyte Pharmaceuticals Inc., 1996.
INC1328219, LIFESEQ™ Clone Information Results, Incyte Pharmaceuticals Inc., 1996.
INC2209486, LIFESEQ™ Clone Information Results, Incyte Pharmaceuticals Inc., 1996.
INC1851527, LIFESEQ™ Clone Information Results, Incyte Pharmaceuticals Inc., 1996.
INC891710, LIFESEQ™ Clone Information Results, Incyte Pharmaceuticals Inc., 1996.
INC1329031, LIFESEQ™ Clone Information Results, Incyte Pharmaceuticals Inc., 1996.
Clone 1329031, LIFESEQ™ Electronic Northern Results, Incyte Pharmaceuticals Inc., 1996.
PANCNOT07, LIFESEQ™ Library Information Results, Incyte Pharmaceuticals Inc., 1996.
LUNGFET03, LIFESEQ™ Library Information Results, Incyte Pharmaceuticals Inc., 1996.
STOMTUT01, LIFESEQ™ Library Information Results, Incyte Pharmaceuticals Inc., 1996.
SINTFET03, LIFESEQ™ Library Information Results, Incyte Pharmaceuticals Inc., 1996.
Strausberg, Accession No. AA530994, Cancer Genome Anatomy Project, 1997.
FLN1329031CB1, LIFESEQ™ Clone Information Results, Incyte Pharmaceuticals Inc., year unknown.
LIN1328219R, LIFESEQ™ Clone Information Results, Incyte Pharmaceuticals Inc., year unknown.
LIN1328219F, LIFESEQ™ Clone Information Results, Incyte Pharmaceuticals Inc., year unknown.
INC3663175, LIFESEQ™ Clone Information Results, Incyte Pharmaceuticals Inc., 1997.
INC3666305, LIFESEQ™ Clone Information Results, Incyte Pharmaceuticals Inc., 1997.
INC3605169, LIFESEQ™ Clone Information Results, Incyte Pharmaceuticals Inc., 1997.
LUNGNOT30, LIFESEQ™ Library Information Results, Incyte Pharmaceuticals Inc., 1997.
PANCNOT16, LIFESEQ™ Library Information Results, Incyte Pharmaceuticals Inc., 1997.
Miller et al., "Structure-function studies of motilin analogues," *Peptides* 16(1): 11-18, 1995.
Peeters. et al., "D-Amino Acid and Alanine Scans of the Bioactive Portion of Porcine Motilin," *Peptides* 13:1103-1107, 1992.
Macielag et al., "Substitution of Pro$^3$ in (Leu$^{13}$) Motilin Affords Antagonists to the GI Motilin Receptor," *Peptides: Chemistry, Structure and Biology*: 659-660, 1996.

(Continued)

*Primary Examiner* — Bao Li
(74) *Attorney, Agent, or Firm* — Todd Spalding

(57) ABSTRACT

The present invention relates to a method of forming a peptide-receptor complex with zsig33 polypeptides and their receptors as well as antibodies. Methods of modulating gastric contractility, nutrient uptake, growth hormones, the secretion of digestive enzymes and hormones, and/or secretion of enzymes and/or hormones in the pancreas are also included.

17 Claims, No Drawings

OTHER PUBLICATIONS

Rhee et al., "Regulation of Phosphoinositide-specific Phospholipase C Isozymes," *J. Biol. Chem.* 272(24): 15045-15048, 1997.

Bowie et al., "Deciphering the Message in Protein Sequences: Tolerance to Amino Acid Substitutions," *Science 247*: 1306-1310, 1990.

George et al., "Macromolecular Sequencing and Synthesis, Selected Methods and Applications" Alan R. Liss, Inc, New York, Schlessinger D. (Ed), pp. 127-149, 1988.

Barton, "Protein Structure Prediction: A Practical Approach" IRL Press at Oxford Univ., Sternberg K. (Ed); pp. 31-63, 1997.

Harlow et al., "Antibodies: A Laboratory Manual" Cold Spring Harbor, NY Publisher: Cold Srpung Harbor Laboratory, 1988.

Benjamini et al., "Immunology: A Short Course" 2$^{nd}$ ed. Publisher: Wiley-Liss, N.Y., p. 40, 1991.

Alberts et al., "Molecular Biology of the Cell", 3$^{rd}$ ed. Publisher: Garland Publishing, Inc. N.Y. p. 119, 1994.

Daniel et al., "Mapping of Linear Antigenic Sites on the S Glycoprotein of a Neurotropic Murine coronavirus with Synthetic Peptides: A Combination of Nine Prediction Algorithms Fails to Identify Relevant Epitopes and Peptide Immunogenicity is Drastically Influenced by the Nature of the Protein Carrier," *Virology 202*: 540-549, 1994.

Nataro et al., "Aggregative Adherence Fimbria I Expression in Enteroaggregative *Escherichia coli* Requires Two Unlinked Plasmid Regions," *Infection and Immunity 61*(3): 1126-1131, Mar. 1993.

Sambrook, J. et al., "Molecular Cloning: A Laboratory Manual" 2$^{nd}$ ed. Publisher Cold Spring Harbor Laboratory Press, pp. 18.2-18.10, 1989.

Ngo, J, et al., "The Protein Folding Problem and Tertiary Structure Prediction", Merz and Le Grand (Eds) Springer Verlag, 433, 492-495, (1994).

Kai et al., "Studies on Peptides. LV.[1,2] Total Synthesis of Porcine Motilin, a Gastric Motor Activity Stimulating Polypeptide," *Chem. Pharm. Bull.* (23)10: 2346-2352 (1975).

Sakai et al., "Autoradiographic study of motilin binding sites in the rabbit gastrointestinal tract," *Regul. Pept 53*: 249-257, 1994.

Bormans et al., "Motilin receptors in rabbit stomach and small intestine," *Regul. Pept 15*: 143-153, 1986.

Hasler et al., "Erythromycin contracts rabit colon myocytes via occupation of motilin receptors," *Am. J. Physiol. 262* (1 Pt1): G 50-55, 1992.

Depoortere et al., "Motilin Receptors of the Rabbin Colon," *Peptides 12*: 89-94, 1991.

Koutsoviti-Papadopoulou et al., "Effect of Erythromycin on Different Parts of the Rabbit Intestine: Comparison with Motilin," *Gen. Pharmac.* 25(1): 93-96, 1994.

Rehfeld and Hansen, "Characterization of Preprocholecystokinin Products in the Porcine Cerebral Cortex," *J. Biol. Chem.* 261(13): 5832-5840, 1986.

Rehfeld and Johnsen, "Identification of gastrin component I as gastrin-71: The largest possible bioactive progastrin product," *Eur. J. Biochem. 223*: 765-773, 1994.

Franks, "Protein Biotechnology: Isolation, Characterization, and Stabilization." Publisher: Humana Press, New Jersey, 1993.

Beacham et al., "Peptides," Publisher: North-Holland Publishing Company, Amsterdam, pp. 235-241, 1967.

Christ et al., "Human Secretin: Biologic Effects and Plasma Kinetics in Humans," *Gastroenterology 94*: 311-316, 1988.

Cunningham et al., "High-Resolution Epitope Mapping of hGH-Receptor Interactions by Alanine-Scanning Mutagenesis," *Science 244*: 1081-1085, 1989.

Sheppard et al., U.S. Appl. No. 09/718,803, filed Nov. 22, 2000.

SEQUENCE LISTING

```
<160> NUMBER OF SEQ ID NOS: 16

<210> SEQ ID NO 1
<211> LENGTH: 351
<212> TYPE: DNA
<213> ORGANISM: Homo sapiens
<220> FEATURE:
<221> NAME/KEY: CDS
<222> LOCATION: (1)...(351)

<400> SEQUENCE: 1 atg ccc tcc cca ggg acc gtc tgc agc ctc ctg ctc ctc ggc atg ctc    48
Met Pro Ser Pro Gly Thr Val Cys Ser Leu Leu Leu Leu Gly Met Leu
1               5                   10                  15 tgg ctg gac ttg gcc atg gca ggc tcc agc ttc ctg agc cct gaa cac    96
Trp Leu Asp Leu Ala Met Ala Gly Ser Ser Phe Leu Ser Pro Glu His
            20                  25                  30 cag aga gtc cag cag aga aag gag tcg aag aag cca cca gcc aag ctg   144
Gln Arg Val Gln Gln Arg Lys Glu Ser Lys Lys Pro Pro Ala Lys Leu
        35                  40                  45 cag ccc cga gct cta gca ggc tgg ctc cgc ccg gaa gat gga ggt caa   192
Gln Pro Arg Ala Leu Ala Gly Trp Leu Arg Pro Glu Asp Gly Gly Gln
    50                  55                  60
```

```
gca gaa ggg gca gag gat gaa ctg gaa gtc cgg ttc aac gcc ccc ttt    240
Ala Glu Gly Ala Glu Asp Glu Leu Glu Val Arg Phe Asn Ala Pro Phe
 65                  70                  75                  80 gat gtt gga atc aag ctg tca ggg gtt cag tac cag cag cac agc cag    288
Asp Val Gly Ile Lys Leu Ser Gly Val Gln Tyr Gln Gln His Ser Gln
                 85                  90                  95 gcc ctg ggg aag ttt ctt cag gac atc ctc tgg gaa gag gcc aaa gag    336
Ala Leu Gly Lys Phe Leu Gln Asp Ile Leu Trp Glu Glu Ala Lys Glu
            100                 105                 110 gcc cca gcc gac aag                                                351
Ala Pro Ala Asp Lys
        115

<210> SEQ ID NO 2
<211> LENGTH: 117
<212> TYPE: PRT
<213> ORGANISM: Homo sapiens

<400> SEQUENCE: 2

Met Pro Ser Pro Gly Thr Val Cys Ser Leu Leu Leu Leu Gly Met Leu
  1               5                  10                  15

Trp Leu Asp Leu Ala Met Ala Gly Ser Ser Phe Leu Ser Pro Glu His
                 20                  25                  30

Gln Arg Val Gln Gln Arg Lys Glu Ser Lys Lys Pro Pro Ala Lys Leu
             35                  40                  45

Gln Pro Arg Ala Leu Ala Gly Trp Leu Arg Pro Glu Asp Gly Gly Gln
         50                  55                  60

Ala Glu Gly Ala Glu Asp Glu Leu Glu Val Arg Phe Asn Ala Pro Phe
 65                  70                  75                  80

Asp Val Gly Ile Lys Leu Ser Gly Val Gln Tyr Gln Gln His Ser Gln
                 85                  90                  95

Ala Leu Gly Lys Phe Leu Gln Asp Ile Leu Trp Glu Glu Ala Lys Glu
            100                 105                 110

Ala Pro Ala Asp Lys
        115

<210> SEQ ID NO 3
<211> LENGTH: 351
<212> TYPE: DNA
<213> ORGANISM: Artificial Sequence
<220> FEATURE:
<223> OTHER INFORMATION: Computationally derived degenerate
      polynucleotide
<220> FEATURE:
<221> NAME/KEY: misc_feature
<222> LOCATION: (1)...(351)
<223> OTHER INFORMATION: n = A,T,C or G

<400> SEQUENCE: 3
atgccnwsnc cnggnacngt ntgywsnytn ytnytnytng gnatgytntg gytngayytn     60
gcnatggcng gnwsnwsntt yytnwsnccn garcaycarm gngtncarca rmgnaargar    120
wsnaaraarc cnccngcnaa rytncarccn mgngcnytng cnggntggyt nmgnccngar    180
gayggnggnc argcngargg ncgngargay garytngarg tnmgnttyaa ygcnccnttty   240 gaygtnggna thaarytnws nggngtncar taycarcarc aywsncargc nytnggnaar    300
ttyytncarg ayathytntg ggargargcn aargargcnc cngcngayaa r             351

<210> SEQ ID NO 4
<211> LENGTH: 1101
<212> TYPE: DNA
<213> ORGANISM: Homo sapiens
```

```
<220> FEATURE:
<221> NAME/KEY: CDS
<222> LOCATION: (1)...(1101)

<400> SEQUENCE: 4 atg tgg aac gcg acg ccc agc gaa gag ccg ggg ttc aac ctc aca ctg      48
Met Trp Asn Ala Thr Pro Ser Glu Glu Pro Gly Phe Asn Leu Thr Leu
1               5                   10                  15 gcc gac ctg gac tgg gat gct tcc ccc ggc aac gac tcg ctg ggc gac      96
Ala Asp Leu Asp Trp Asp Ala Ser Pro Gly Asn Asp Ser Leu Gly Asp
            20                  25                  30 gag ctg ctg cag ctc ttc ccc gcg ccg ctg ctg gcg ggc gtc aca gcc     144
Glu Leu Leu Gln Leu Phe Pro Ala Pro Leu Leu Ala Gly Val Thr Ala
        35                  40                  45 acc tgc gtg gca ctc ttc gtg gtg ggt atc gct ggc aac ctc ctc acc     192
Thr Cys Val Ala Leu Phe Val Val Gly Ile Ala Gly Asn Leu Leu Thr
    50                  55                  60 atg ctg gtg gtg tcg cgc ttc cgc gag ctg cgc acc acc acc aac ctc     240
Met Leu Val Val Ser Arg Phe Arg Glu Leu Arg Thr Thr Thr Asn Leu
65                  70                  75                  80 tac ctg tcc agc atg gcc ttc tcc gat ctg ctc atc ttc ctc tgc atg     288
Tyr Leu Ser Ser Met Ala Phe Ser Asp Leu Leu Ile Phe Leu Cys Met
                85                  90                  95 ccc ctg gac ctc gtt cgc ctc tgg cag tac cgg ccc tgg aac ttc ggc     336
Pro Leu Asp Leu Val Arg Leu Trp Gln Tyr Arg Pro Trp Asn Phe Gly
            100                 105                 110 gac ctc ctc tgc aaa ctc ttc caa ttc gtc agt gag agc tgc acc tac     384
Asp Leu Leu Cys Lys Leu Phe Gln Phe Val Ser Glu Ser Cys Thr Tyr
        115                 120                 125 gcc acg gtg ctc acc atc aca gcg ctg agc gtc gag cgc tac ttc gcc     432
Ala Thr Val Leu Thr Ile Thr Ala Leu Ser Val Glu Arg Tyr Phe Ala
    130                 135                 140 atc tgc ttc cca ctc cgg gcc aag gtg gtg gtc acc aag ggg cgg gtg     480
Ile Cys Phe Pro Leu Arg Ala Lys Val Val Val Thr Lys Gly Arg Val
145                 150                 155                 160 aag ctg gtc atc ttc gtc atc tgg gcc gtg gcc ttc tgc agc gcc ggg     528
Lys Leu Val Ile Phe Val Ile Trp Ala Val Ala Phe Cys Ser Ala Gly
                165                 170                 175 ccc atc ttc gtg cta gtc ggg gtg gag cac gag aac ggc acc gac cct     576
Pro Ile Phe Val Leu Val Gly Val Glu His Glu Asn Gly Thr Asp Pro
            180                 185                 190 tgg gac acc aac gag tgc cgc ccc acc gag ttt gcg gtg cgc tct gga     624
Trp Asp Thr Asn Glu Cys Arg Pro Thr Glu Phe Ala Val Arg Ser Gly
        195                 200                 205 ctg ctc acg gtc atg gtg tgg gtg tcc agc atc ttc ttc ctt cct         672
Leu Leu Thr Val Met Val Trp Val Ser Ser Ile Phe Phe Leu Pro
    210                 215                 220 gtc ttc tgt ctc acg gtc ctc tac agt ctc atc ggc agg aag ctg tgg     720
Val Phe Cys Leu Thr Val Leu Tyr Ser Leu Ile Gly Arg Lys Leu Trp
225                 230                 235                 240 cgg agg agg cgc ggc gat gct gtc gtg ggt gcc tcg ctc agg gac cag     768
Arg Arg Arg Arg Gly Asp Ala Val Val Gly Ala Ser Leu Arg Asp Gln
                245                 250                 255 aac cac aag caa acc gtg aaa atg ctg gct gta gtg gtg ttt gcc ttc     816
Asn His Lys Gln Thr Val Lys Met Leu Ala Val Val Val Phe Ala Phe
            260                 265                 270 atc ctc tgc tgg ctc ccc ttc cac gta ggg cga tat tta ttt tcc aaa     864
Ile Leu Cys Trp Leu Pro Phe His Val Gly Arg Tyr Leu Phe Ser Lys
        275                 280                 285 tcc ttt gag cct ggc tcc ttg gag att gct cag atc agc cag tac tgc     912
Ser Phe Glu Pro Gly Ser Leu Glu Ile Ala Gln Ile Ser Gln Tyr Cys
```

```
               290                 295                 300
aac ctc gtg tcc ttt gtc ctc ttc tac ctc agt gct gcc atc aac ccc    960
Asn Leu Val Ser Phe Val Leu Phe Tyr Leu Ser Ala Ala Ile Asn Pro
305                 310                 315                 320 att ctg tac aac atc atg tcc aag aag tac cgg gtg gca gtg ttc aga   1008
Ile Leu Tyr Asn Ile Met Ser Lys Lys Tyr Arg Val Ala Val Phe Arg
                325                 330                 335 ctt ctg gga ttc gaa ccc ttc tcc cag aga aag ctc tcc act ctg aaa   1056
Leu Leu Gly Phe Glu Pro Phe Ser Gln Arg Lys Leu Ser Thr Leu Lys
            340                 345                 350 gat gaa agt tct cgg gcc tgg aca gaa tct agt att aat aca tga       1101
Asp Glu Ser Ser Arg Ala Trp Thr Glu Ser Ser Ile Asn Thr *
        355                 360                 365
```

<210> SEQ ID NO 5
<211> LENGTH: 366
<212> TYPE: PRT
<213> ORGANISM: Homo sapiens

<400> SEQUENCE: 5

```
Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Ala Val Val Val Phe Ala Phe
            260                 265                 270

Ile Leu Cys Trp Leu Pro Phe His Val Gly Arg Tyr Leu Phe Ser Lys
        275                 280                 285
```

```
Ser Phe Glu Pro Gly Ser Leu Glu Ile Ala Gln Ile Ser Gln Tyr Cys
            290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
                325                 330                 335

Leu Leu Gly Phe Glu Pro Phe Ser Gln Arg Lys Leu Ser Thr Leu Lys
                340                 345                 350

Asp Glu Ser Ser Arg Ala Trp Thr Glu Ser Ser Ile Asn Thr
                355                 360                 365

<210> SEQ ID NO 6
<211> LENGTH: 1098
<212> TYPE: DNA
<213> ORGANISM: Artificial Sequence
<220> FEATURE:
<223> OTHER INFORMATION: Computationally derived degenerate sequence
<220> FEATURE:
<221> NAME/KEY: misc_feature
<222> LOCATION: (1)...(1098)
<223> OTHER INFORMATION: n = A,T,C or G

<400> SEQUENCE: 6
atgtggaayg cnacnccnws ngargarccn ggnttyaayy tnacnytngc ngayytngay      60
tgggaygcnw snccnggnaa ygaywsnytn ggngaygary tnytncaryt nttyccngcn     120
ccnytnytng cnggngtnac ngcnacntgy gtngcnytnt tygtngtngg nathgcnggn     180
aayytnytna cnatgytngt ngtnwsnmgn ttymgngary tnmgnacnac nacnaayytn     240
tayytnwsnw snatggcntt ywsngayytn ytnathttyy tntgyatgcc nytngayytn     300
gtnmgnytnt ggcartaymg nccntggaay ttyggngayy tnytntgyaa rytnttycar     360
ttygtnwsng arwsntgyac ntaygcnacn gtnytnacna thacngcnyt nwsngtngar     420
mgntayttyg cnathtgytt yccnytnmgn gcnaargtng tgtnacnaa rggnmgngtn     480
aarytngtna thttygtnat htgggcngtn gcnttytgyw sngcnggncc nathttygtn     540
ytngtnggng tngarcayga raayggnacn gayccntggg ayacnaayga rtgymgnccn     600
acngarttyg cngtnmgnws nggnytnytn acngtnatgg tntgggtnws nwsnathtty     660
ttyttyytnc cngtnttytg yytnacngtn ytntaywsny tnathggnmg naarytntgg     720
mgnmgnmgnm gnggngaygc ngtngtnggn gcnwsnytnm gngaycaraa ycayaarcar     780
acngtnaara tgytngcgt ngtngtntty gcnttyathy tngytggyt nccnttycay     840
gtnggnmgnt ayytnttyws naarwsntty garccnggnw snytngarat hgcncarath     900
wsncartayt gyaayytngt nwsnttygtn ytnttytayy tnwsngcngc nathaayccn     960
athytntaya ayathatgws naaraartay mgngtngcng tnttymgnyt nytnggntty    1020
garccnttyw sncarmgnaa rytnwsnacn ytnaargayg arwsnwsnmg ngcntggacn    1080
garwsnwsna thaayacn                                                  1098

<210> SEQ ID NO 7
<211> LENGTH: 546
<212> TYPE: DNA
<213> ORGANISM: Sus scrofa
<220> FEATURE:
<221> NAME/KEY: CDS
<222> LOCATION: (40)...(396)

<400> SEQUENCE: 7
gggcagagac acacacgcgc ccagttgtcc agctccagg atg gtg tcc cgc aag          54
                                            Met Val Ser Arg Lys
```

```
                           1               5
gct gtg gtc gtc ctg ctg gtg gtg cac gca gct gcc atg ctg gcc tcc    102
Ala Val Val Val Leu Leu Val Val His Ala Ala Ala Met Leu Ala Ser
                10              15                  20 cac acg gaa gcc ttt gtt ccc agc ttt acc tac ggg gaa ctt cag agg    150
His Thr Glu Ala Phe Val Pro Ser Phe Thr Tyr Gly Glu Leu Gln Arg
            25                  30                  35 atg cag gaa aag gag cgg aat aaa ggg caa aag aaa tcc ctg agt gtc    198
Met Gln Glu Lys Glu Arg Asn Lys Gly Gln Lys Lys Ser Leu Ser Val
        40                  45                  50 cag cag gcg tcg gag gag ctc ggc cct ctg gac ccc tcg gag ccc acg    246
Gln Gln Ala Ser Glu Glu Leu Gly Pro Leu Asp Pro Ser Glu Pro Thr
    55                  60                  65 aag gaa gaa gaa agg gtg gtt atc aag ctg ctc gcg cct gtg gac att    294
Lys Glu Glu Glu Arg Val Val Ile Lys Leu Leu Ala Pro Val Asp Ile
70                  75                  80                  85 gga atc agg atg gac tcc agg cag ctg gaa aag tac cgg gcc acc ctg    342
Gly Ile Arg Met Asp Ser Arg Gln Leu Glu Lys Tyr Arg Ala Thr Leu
                90                  95                  100 gaa agg ctg ctg ggc cag gcg ccg cag tcc acc cag aac cag aat gcc    390
Glu Arg Leu Leu Gly Gln Ala Pro Gln Ser Thr Gln Asn Gln Asn Ala
            105                 110                 115 gcc aag taacaggccg ctgggggaga aggaggacac agctcggacc ccctcccac      446
Ala Lys gcagggaggg cctagaaatc cgctgggctt ggaaggaaaa caccctctcc caaacagccc   506
tcagcccccc tccccagca aataaagcgt ggaaataggc                         546
```

<210> SEQ ID NO 8
<211> LENGTH: 119
<212> TYPE: PRT
<213> ORGANISM: Sus scrofa

<400> SEQUENCE: 8

```
Met Val Ser Arg Lys Ala Val Val Leu Val Val His Ala Ala
1               5                   10                  15

Ala Met Leu Ala Ser His Thr Glu Ala Phe Val Pro Ser Phe Thr Tyr
            20                  25                  30

Gly Glu Leu Gln Arg Met Gln Glu Lys Glu Arg Asn Lys Gly Gln Lys
        35                  40                  45

Lys Ser Leu Ser Val Gln Gln Ala Ser Glu Glu Leu Gly Pro Leu Asp
    50                  55                  60

Pro Ser Glu Pro Thr Lys Glu Glu Glu Arg Val Val Ile Lys Leu Leu
65                  70                  75                  80

Ala Pro Val Asp Ile Gly Ile Arg Met Asp Ser Arg Gln Leu Glu Lys
                85                  90                  95

Tyr Arg Ala Thr Leu Glu Arg Leu Leu Gly Gln Ala Pro Gln Ser Thr
            100                 105                 110

Gln Asn Gln Asn Ala Ala Lys
        115
```

<210> SEQ ID NO 9
<211> LENGTH: 1239
<212> TYPE: DNA
<213> ORGANISM: Homo sapiens
<220> FEATURE:
<221> NAME/KEY: CDS
<222> LOCATION: (1)...(1239)

<400> SEQUENCE: 9

```
atg ggc agc ccc tgg aac ggc agc gac ggc ccc gag ggg gcg cgg gag      48
Met Gly Ser Pro Trp Asn Gly Ser Asp Gly Pro Glu Gly Ala Arg Glu
1               5                   10                  15 ccg ccg tgg ccc gcg ctg ccg cct tgc gac gag cgc cgc tgc tcg ccc      96
Pro Pro Trp Pro Ala Leu Pro Pro Cys Asp Glu Arg Arg Cys Ser Pro
                20                  25                  30 ttt ccc ctg ggg gcg ctg gtg ccg gtg acc gct gtg tgc ctg tgc ctg     144
Phe Pro Leu Gly Ala Leu Val Pro Val Thr Ala Val Cys Leu Cys Leu
            35                  40                  45 ttc gtc gtc ggg gtg agc ggc aac gtg gtg acc gtg atg ctg atc ggg     192
Phe Val Val Gly Val Ser Gly Asn Val Val Thr Val Met Leu Ile Gly
50                  55                  60 cgc tac cgg gac atg cgg acc acc acc aac ttg tac ctg ggc agc atg     240
Arg Tyr Arg Asp Met Arg Thr Thr Thr Asn Leu Tyr Leu Gly Ser Met
65              70                  75                  80 gcc gtg tcc gac cta ctc atc ctg ctc ggg ctg ccg ttc gac ctg tac     288
Ala Val Ser Asp Leu Leu Ile Leu Leu Gly Leu Pro Phe Asp Leu Tyr
                85                  90                  95 cgc ctc tgg cgc tcg cgg ccc tgg gtg ttc ggg ccg ctg ctc tgc cgc     336
Arg Leu Trp Arg Ser Arg Pro Trp Val Phe Gly Pro Leu Leu Cys Arg
                100                 105                 110 ctg tcc ctc tac gtg ggc gag ggc tgc acc tac gcc acg ctg ctg cac     384
Leu Ser Leu Tyr Val Gly Glu Gly Cys Thr Tyr Ala Thr Leu Leu His
            115                 120                 125 atg acc gcg ctc agc gtc gag cgc tac ctg gcc atc tgc cgc ccg ctc     432
Met Thr Ala Leu Ser Val Glu Arg Tyr Leu Ala Ile Cys Arg Pro Leu
130                 135                 140 cgc gcc cgc gtc ttg gtc acc cgg cgc cgc gtc cgc gcg ctc atc gct     480
Arg Ala Arg Val Leu Val Thr Arg Arg Arg Val Arg Ala Leu Ile Ala
145                 150                 155                 160 gtg ctc tgg gcc gtg gcg ctg ctc tct gcc ggt ccc ttc ttg ttc ctg     528
Val Leu Trp Ala Val Ala Leu Leu Ser Ala Gly Pro Phe Leu Phe Leu
                165                 170                 175 gtg ggc gtc gag cag gac ccc ggc atc tcc gta gtc ccg ggc ctc aat     576
Val Gly Val Glu Gln Asp Pro Gly Ile Ser Val Val Pro Gly Leu Asn
                180                 185                 190 ggc acc gcg cgg atc gcc tcc tcg cct ctc gcc tcg tcg ccg cct ctc     624
Gly Thr Ala Arg Ile Ala Ser Ser Pro Leu Ala Ser Ser Pro Pro Leu
            195                 200                 205 tgg ctc tcg cgg gcg cca ccg ccg tcc ccg ccg tcg ggg ccc gag acc     672
Trp Leu Ser Arg Ala Pro Pro Pro Ser Pro Pro Ser Gly Pro Glu Thr
210                 215                 220 gcg gag gcc gcg gcg ctg ttc agc cgc gaa tgc cgg ccg agc ccc gcg     720
Ala Glu Ala Ala Ala Leu Phe Ser Arg Glu Cys Arg Pro Ser Pro Ala
225                 230                 235                 240 cag ctg ggc gcg ctg cgt gtc atg ctg tgg gtc acc acc gcc tac ttc     768
Gln Leu Gly Ala Leu Arg Val Met Leu Trp Val Thr Thr Ala Tyr Phe
                245                 250                 255 ttc ctg ccc ttt ctg tgc ctc agc atc ctc tac ggg ctc atc ggg cgg     816
Phe Leu Pro Phe Leu Cys Leu Ser Ile Leu Tyr Gly Leu Ile Gly Arg
                260                 265                 270 gag ctg tgg agc agc cgg cgg ccg ctg cga ggg ccg gcc gcc tcg ggg     864
Glu Leu Trp Ser Ser Arg Arg Pro Leu Arg Gly Pro Ala Ala Ser Gly
            275                 280                 285 cgg gag aga ggc cac cgg cag acc gtc cgc gtc ctg ctg gtg gtg gtt     912
Arg Glu Arg Gly His Arg Gln Thr Val Arg Val Leu Leu Val Val Val
290                 295                 300 ctg gca ttt ata att tgc tgg ttg ccc ttc cac gtt ggc aga atc att     960
Leu Ala Phe Ile Ile Cys Trp Leu Pro Phe His Val Gly Arg Ile Ile
305                 310                 315                 320
```

```
tac ata aac acg gaa gat tcg cgg atg atg tac ttc tct cag tac ttt    1008
Tyr Ile Asn Thr Glu Asp Ser Arg Met Met Tyr Phe Ser Gln Tyr Phe
                325                 330                 335 aac atc gtc gct ctg caa ctt ttc tat ctg agc gca tct atc aac cca    1056
Asn Ile Val Ala Leu Gln Leu Phe Tyr Leu Ser Ala Ser Ile Asn Pro
            340                 345                 350 atc ctc tac aac ctc att tca aag aag tac aga gcg gcg gcc ttt aaa    1104
Ile Leu Tyr Asn Leu Ile Ser Lys Lys Tyr Arg Ala Ala Ala Phe Lys
        355                 360                 365 ctg ctg ctc gca agg aag tcc agg ccg aga ggc ttc cac aga agc agg    1152
Leu Leu Leu Ala Arg Lys Ser Arg Pro Arg Gly Phe His Arg Ser Arg
    370                 375                 380 gac act gcg ggg gaa gtt gca ggg gac act gga gga gac acg gtg ggc    1200
Asp Thr Ala Gly Glu Val Ala Gly Asp Thr Gly Gly Asp Thr Val Gly
385                 390                 395                 400 tac acc gag aca agc gct aac gtg aag acg atg gga taa                1239
Tyr Thr Glu Thr Ser Ala Asn Val Lys Thr Met Gly  *
                405                 410

<210> SEQ ID NO 10
<211> LENGTH: 412
<212> TYPE: PRT
<213> ORGANISM: Homo sapiens

<400> SEQUENCE: 10

Met Gly Ser Pro Trp Asn Gly Ser Asp Gly Pro Glu Gly Ala Arg Glu
 1               5                  10                  15

Pro Pro Trp Pro Ala Leu Pro Pro Cys Asp Glu Arg Arg Cys Ser Pro
             20                  25                  30

Phe Pro Leu Gly Ala Leu Val Pro Val Thr Ala Val Cys Leu Cys Leu
         35                  40                  45

Phe Val Val Gly Val Ser Gly Asn Val Val Thr Val Met Leu Ile Gly
     50                  55                  60

Arg Tyr Arg Asp Met Arg Thr Thr Thr Asn Leu Tyr Leu Gly Ser Met
65                  70                  75                  80

Ala Val Ser Asp Leu Leu Ile Leu Leu Gly Leu Pro Phe Asp Leu Tyr
                 85                  90                  95

Arg Leu Trp Arg Ser Arg Pro Trp Val Phe Gly Pro Leu Leu Cys Arg
            100                 105                 110

Leu Ser Leu Tyr Val Gly Glu Gly Cys Thr Tyr Ala Thr Leu Leu His
        115                 120                 125

Met Thr Ala Leu Ser Val Glu Arg Tyr Leu Ala Ile Cys Arg Pro Leu
    130                 135                 140

Arg Ala Arg Val Leu Val Thr Arg Arg Arg Val Arg Ala Leu Ile Ala
145                 150                 155                 160

Val Leu Trp Ala Val Ala Leu Leu Ser Ala Gly Pro Phe Leu Phe Leu
                165                 170                 175

Val Gly Val Glu Gln Asp Pro Gly Ile Ser Val Val Pro Gly Leu Asn
            180                 185                 190

Gly Thr Ala Arg Ile Ala Ser Ser Pro Leu Ala Ser Ser Pro Pro Leu
        195                 200                 205

Trp Leu Ser Arg Ala Pro Pro Pro Ser Pro Ser Gly Pro Glu Thr
    210                 215                 220

Ala Glu Ala Ala Ala Leu Phe Ser Arg Glu Cys Arg Pro Ser Pro Ala
225                 230                 235                 240

Gln Leu Gly Ala Leu Arg Val Met Leu Trp Val Thr Thr Ala Tyr Phe
                245                 250                 255
```

```
Phe Leu Pro Phe Leu Cys Leu Ser Ile Leu Tyr Gly Leu Ile Gly Arg
                260                 265                 270

Glu Leu Trp Ser Ser Arg Arg Pro Leu Arg Gly Pro Ala Ala Ser Gly
            275                 280                 285

Arg Glu Arg Gly His Arg Gln Thr Val Arg Val Leu Val Val Val
        290                 295                 300

Leu Ala Phe Ile Ile Cys Trp Leu Pro Phe His Val Gly Arg Ile Ile
305                 310                 315                 320

Tyr Ile Asn Thr Glu Asp Ser Arg Met Met Tyr Phe Ser Gln Tyr Phe
                325                 330                 335

Asn Ile Val Ala Leu Gln Leu Phe Tyr Leu Ser Ala Ser Ile Asn Pro
            340                 345                 350

Ile Leu Tyr Asn Leu Ile Ser Lys Lys Tyr Arg Ala Ala Ala Phe Lys
        355                 360                 365

Leu Leu Leu Ala Arg Lys Ser Arg Pro Arg Gly Phe His Arg Ser Arg
370                 375                 380

Asp Thr Ala Gly Glu Val Ala Gly Asp Thr Gly Gly Asp Thr Val Gly
385                 390                 395                 400

Tyr Thr Glu Thr Ser Ala Asn Val Lys Thr Met Gly
                405                 410

<210> SEQ ID NO 11
<211> LENGTH: 1161
<212> TYPE: DNA
<213> ORGANISM: Homo sapiens
<220> FEATURE:
<221> NAME/KEY: CDS
<222> LOCATION: (1)...(1161)

<400> SEQUENCE: 11 atg ggc agc ccc tgg aac ggc agc gac ggc ccc gag ggg gcg cgg gag      48
Met Gly Ser Pro Trp Asn Gly Ser Asp Gly Pro Glu Gly Ala Arg Glu
1               5                   10                  15 ccg ccg tgg ccc gcg ctg ccg cct tgc gac gag cgc cgc tgc tcg ccc      96
Pro Pro Trp Pro Ala Leu Pro Pro Cys Asp Glu Arg Arg Cys Ser Pro
            20                  25                  30 ttt ccc ctg ggg gcg ctg gtg ccg gtg acc gct gtg tgc ctg tgc ctg     144
Phe Pro Leu Gly Ala Leu Val Pro Val Thr Ala Val Cys Leu Cys Leu
        35                  40                  45 ttc gtc gtc ggg gtg agc ggc aac gtg gtg acc gtg atg ctg atc ggg     192
Phe Val Val Gly Val Ser Gly Asn Val Val Thr Val Met Leu Ile Gly
    50                  55                  60 cgc tac cgg gac atg cgg acc acc acc aac ttg tac ctg ggc agc atg     240
Arg Tyr Arg Asp Met Arg Thr Thr Thr Asn Leu Tyr Leu Gly Ser Met
65                  70                  75                  80 gcc gtg tcc gac cta ctc atc ctg ctc ggg ctg ccg ttc gac ctg tac     288
Ala Val Ser Asp Leu Leu Ile Leu Leu Gly Leu Pro Phe Asp Leu Tyr
                85                  90                  95 cgc ctc tgg cgc tcg cgg ccc tgg gtg ttc ggg ccg ctc tgc cgc         336
Arg Leu Trp Arg Ser Arg Pro Trp Val Phe Gly Pro Leu Cys Arg
            100                 105                 110 ctg tcc ctc tac gtg ggc gag ggc tgc acc tac gcc acg ctg ctg cac     384
Leu Ser Leu Tyr Val Gly Glu Gly Cys Thr Tyr Ala Thr Leu Leu His
        115                 120                 125 atg acc gcg ctc agc gtc gag cgc tac ctg gcc atc tgc cgc ccg ctc     432
Met Thr Ala Leu Ser Val Glu Arg Tyr Leu Ala Ile Cys Arg Pro Leu
    130                 135                 140 cgc gcc cgc gtc ttg gtc acc cgg cgc cgc gtc cgc gcg ctc atc gct     480
Arg Ala Arg Val Leu Val Thr Arg Arg Arg Val Arg Ala Leu Ile Ala
145                 150                 155                 160
```

```
gtg ctc tgg gcc gtg gcg ctg ctc tct gcc ggt ccc ttc ttg ttc ctg          528
Val Leu Trp Ala Val Ala Leu Leu Ser Ala Gly Pro Phe Leu Phe Leu
            165                 170                 175 gtg ggc gtc gag cag gac ccc ggc atc tcc gta gtc ccg ggc ctc aat          576
Val Gly Val Glu Gln Asp Pro Gly Ile Ser Val Val Pro Gly Leu Asn
        180                 185                 190 ggc acc gcg cgg atc gcc tcc tcg cct ctc gcc tcg tcg ccg cct ctc          624
Gly Thr Ala Arg Ile Ala Ser Ser Pro Leu Ala Ser Ser Pro Pro Leu
    195                 200                 205 tgg ctc tcg cgg gcg cca ccc ccg tcc ccg ccg tcg ggg ccc gag acc          672
Trp Leu Ser Arg Ala Pro Pro Pro Ser Pro Pro Ser Gly Pro Glu Thr
210                 215                 220 gcg gag gcc gcg gcg ctg ttc agc cgc gaa tgc cgg ccg agc ccc gcg          720
Ala Glu Ala Ala Ala Leu Phe Ser Arg Glu Cys Arg Pro Ser Pro Ala
225                 230                 235                 240 cag ctg ggc gcg ctg cgt gtc atg ctg tgg gtc acc acc gcc tac ttc          768
Gln Leu Gly Ala Leu Arg Val Met Leu Trp Val Thr Thr Ala Tyr Phe
            245                 250                 255 ttc ctg ccc ttt ctg tgc ctc agc atc ctc tac ggg ctc atc ggg cgg          816
Phe Leu Pro Phe Leu Cys Leu Ser Ile Leu Tyr Gly Leu Ile Gly Arg
        260                 265                 270 gag ctg tgg agc agc cgg cgg ccg ctg cga ggc ccg gcc gcc tcg ggg          864
Glu Leu Trp Ser Ser Arg Arg Pro Leu Arg Gly Pro Ala Ala Ser Gly
    275                 280                 285 cgg gag aga ggc cac cgg cag acc gtc cgc gtc ctg cgt aag tgg agc          912
Arg Glu Arg Gly His Arg Gln Thr Val Arg Val Leu Arg Lys Trp Ser
290                 295                 300 cgc cgt ggt tcc aaa gac gcc tgc ctg cag tcc gcc ccg ccg ggg acc          960
Arg Arg Gly Ser Lys Asp Ala Cys Leu Gln Ser Ala Pro Pro Gly Thr
305                 310                 315                 320 gcg caa acg ctg ggt ccc ctt ccc ctg ctc gcc cag ctc tgg gcg ccg         1008
Ala Gln Thr Leu Gly Pro Leu Pro Leu Leu Ala Gln Leu Trp Ala Pro
            325                 330                 335 ctt cca gct ccc ttt cct att tcg att cca gcc tcc acc cgc cgt ggt         1056
Leu Pro Ala Pro Phe Pro Ile Ser Ile Pro Ala Ser Thr Arg Arg Gly
        340                 345                 350 ggt ggt tct ggc att tat aat ttg ctg gtt gcc ctt cca cgt tgg cag         1104
Gly Gly Ser Gly Ile Tyr Asn Leu Leu Val Ala Leu Pro Arg Trp Gln
    355                 360                 365 aat cat tta cat aaa cac gga aga ttc gcg gat gat gta ctt ctc tca         1152
Asn His Leu His Lys His Gly Arg Phe Ala Asp Asp Val Leu Leu Ser
370                 375                 380 gta ctt taa                                                             1161
Val Leu *
385

<210> SEQ ID NO 12
<211> LENGTH: 386
<212> TYPE: PRT
<213> ORGANISM: Homo sapiens

<400> SEQUENCE: 12

Met Gly Ser Pro Trp Asn Gly Ser Asp Gly Pro Glu Gly Ala Arg Glu
1               5                   10                  15

Pro Pro Trp Pro Ala Leu Pro Pro Cys Asp Glu Arg Arg Cys Ser Pro
            20                  25                  30

Phe Pro Leu Gly Ala Leu Val Pro Val Thr Ala Val Cys Leu Cys Leu
        35                  40                  45

Phe Val Val Gly Val Ser Gly Asn Val Val Thr Val Met Leu Ile Gly
    50                  55                  60
```

Arg Tyr Arg Asp Met Arg Thr Thr Thr Asn Leu Tyr Leu Gly Ser Met
 65                  70                  75                  80

Ala Val Ser Asp Leu Leu Ile Leu Leu Gly Leu Pro Phe Asp Leu Tyr
             85                  90                  95

Arg Leu Trp Arg Ser Arg Pro Trp Val Phe Gly Pro Leu Leu Cys Arg
            100                 105                 110

Leu Ser Leu Tyr Val Gly Glu Gly Cys Thr Tyr Ala Thr Leu Leu His
        115                 120                 125

Met Thr Ala Leu Ser Val Glu Arg Tyr Leu Ala Ile Cys Arg Pro Leu
    130                 135                 140

Arg Ala Arg Val Leu Val Thr Arg Arg Val Arg Ala Leu Ile Ala
145                 150                 155                 160

Val Leu Trp Ala Val Ala Leu Leu Ser Ala Gly Pro Phe Leu Phe Leu
                165                 170                 175

Val Gly Val Glu Gln Asp Pro Gly Ile Ser Val Val Pro Gly Leu Asn
            180                 185                 190

Gly Thr Ala Arg Ile Ala Ser Ser Pro Leu Ala Ser Ser Pro Pro Leu
        195                 200                 205

Trp Leu Ser Arg Ala Pro Pro Ser Pro Ser Gly Pro Glu Thr
    210                 215                 220

Ala Glu Ala Ala Ala Leu Phe Ser Arg Glu Cys Arg Pro Ser Pro Ala
225                 230                 235                 240

Gln Leu Gly Ala Leu Arg Val Met Leu Trp Val Thr Thr Ala Tyr Phe
                245                 250                 255

Phe Leu Pro Phe Leu Cys Leu Ser Ile Leu Tyr Gly Leu Ile Gly Arg
                260                 265                 270

Glu Leu Trp Ser Ser Arg Arg Pro Leu Arg Gly Pro Ala Ala Ser Gly
            275                 280                 285

Arg Glu Arg Gly His Arg Gln Thr Val Arg Val Leu Arg Lys Trp Ser
    290                 295                 300

Arg Arg Gly Ser Lys Asp Ala Cys Leu Gln Ser Ala Pro Pro Gly Thr
305                 310                 315                 320

Ala Gln Thr Leu Gly Pro Leu Pro Leu Leu Ala Gln Leu Trp Ala Pro
                325                 330                 335

Leu Pro Ala Pro Phe Pro Ile Ser Ile Pro Ala Ser Thr Arg Arg Gly
                340                 345                 350

Gly Gly Ser Gly Ile Tyr Asn Leu Leu Val Ala Leu Pro Arg Trp Gln
            355                 360                 365

Asn His Leu His Lys His Gly Arg Phe Ala Asp Asp Val Leu Leu Ser
    370                 375                 380

Val Leu
385

<210> SEQ ID NO 13
<211> LENGTH: 40
<212> TYPE: DNA
<213> ORGANISM: Artificial Sequence
<220> FEATURE:
<223> OTHER INFORMATION: Oligonucleotide primer ZC12,494

<400> SEQUENCE: 13
ttcttcgact cctttctctg ctggactctc tggtgttcag                          40

<210> SEQ ID NO 14
<211> LENGTH: 6
<212> TYPE: PRT

```
<213> ORGANISM: Artificial Sequence
<220> FEATURE:
<223> OTHER INFORMATION: Carboxyl terminal Glu-Glu tag

<400> SEQUENCE: 14

Glu Tyr Met Pro Met Glu
 1               5

<210> SEQ ID NO 15
<211> LENGTH: 14
<212> TYPE: PRT
<213> ORGANISM: Artificial Sequence
<220> FEATURE:
<223> OTHER INFORMATION: Scrabled polypeptide sequence

<400> SEQUENCE: 15

Ser Leu Ser Arg Gln Gly Ser His Gln Phe Pro Gln Glu Val
 1               5                  10

<210> SEQ ID NO 16
<211> LENGTH: 19
<212> TYPE: PRT
<213> ORGANISM: Artificial Sequence
<220> FEATURE:
<223> OTHER INFORMATION: zsig33 fragment with carboxyl terminal cysteine

<400> SEQUENCE: 16

Gly Ser Ser Phe Leu Ser Pro Glu His Gln Arg Val Gln Gln Arg Lys
 1               5                  10                  15

Glu Ser Cys
```

METHODS OF PURIFYING ZSIG33

REFERENCE TO RELATED APPLICATIONS

This application is a divisional of U.S. application Ser. No. 12/147,187, filed Jun. 26, 2008 now U.S. Pat. No. 7,888,056, which is a continuation of U.S. application Ser. No. 09/718,803, filed Nov. 22, 2000, abandoned, which claims the benefit of U.S. Provisional Application Ser. No. 60/166,765 filed on Nov. 22, 1999, all of which are herein incorporated by reference.

BACKGROUND OF THE INVENTION

Many of the regulatory peptides that are important in maintaining nutritional homeostasis are found in the gastrointestinal environment. These peptides may be synthesized in the digestive system and act locally, but can also be active in the brain as well. In addition, the reverse is also found, i.e., peptides are synthesized in the brain, but found to regulate cells in the gastrointestinal tract. This phenomena has been called the "brain-gut axis" and is important for signaling satiety, regulating body temperature and other physiological processes that require feedback between the brain and gut.

Gut peptide hormones including gastrin, cholecystokinin (CCK), secretin, gastric inhibitory peptide (GIP), vasoactive intestinal polypeptide (VIP), motilin, somatostatin, pancreatic peptide (PP), substance P and neuropeptide Y (NPY), use several different mechanisms of action. For example, gastrin, motilin and CCK function as endocrine- and neurocrine-type hormones. Others, such as gastrin and GIP, are thought to act exclusively in an endocrine fashion. Other modes of action include a combination of endocrine, neurocrine and paracrine action (e.g., somatostatin); exclusively neurocrine action (e.g., NPY); and a combination of neurocrine and paracrine actions (e.g., VIP and Substance P). Most of the gut hormone actions are mediated by membrane-bound receptors and activate second messenger systems. For a review of gut peptides see, Mulvihill et al., in *Basic and Clinical Endocrinology*, pp. 551-570, 4th edition Greenspan F. S. and Baxter, J. D. eds., Appleton & Lange, Norwalk, Conn., 1994.

Many of these gut peptides are synthesized as inactive precursor molecules that require multiple peptide cleavages to be activated. The family known as the "glucagon-secretin" family, which includes VIP, gastrin, secretin, motilin, glucagon and galanin, exemplifies peptides regulated by multiple cleavages and post-translational modifications.

Motilin is a 22 amino acid peptide found in gut tissue of mammalian species (Domschke, W., *Digestive Diseases* 22(5):454-461, 1977). The DNA and amino acid sequences for porcine prepromotilin have been identified (U.S. Pat. No. 5,006,469). Motilin has been characterized as a factor capable of increasing gastric motility, affecting the secretory function of the stomach by stimulating pepsin secretion (Brown et al., *Canadian J. of Physiol. Pharmacol.* 49:399-405, 1971), and recent evidence suggests a role in myoelectric regulation of stomach and small intestine. Cyclic increases of motilin have been correlated with phase III of the interdigestive myoelectric complex and the hunger contraction of the duodenum (Chey et al., in *Gut Hormones*, (eds.) Bloom, S. R., pp. 355-358, Edinburgh, Churchill Livingstone, 1978; Lee et al, *Am. J. Digestive Diseases,* 23:789-795, 1978; and Itoh et al., *Am. J. Digestive Diseases,* 23:929-935, 1978). Motilin and analogues of motilin have been demonstrated to produce contraction of gastrointestinal smooth muscle, but not other types of smooth muscle cells (Strunz et al., *Gastroenterology* 68:1485-1491, 1975).

In view of the proven clinical utility of gut hormones, there is a need in the art for additional such molecules for use as both therapeutic agents and research tools and reagents. Gut Hormones are used in the laboratory to study developmental processes, and in laboratory and industry settings as components of cell culture media.

SUMMARY OF THE INVENTION

These and other aspects of the invention will become evident upon reference to the following detailed description of the invention.

Within one aspect of the invention a method is provided for forming a reversible peptide-receptor complex comprising; providing an immobilized receptor; and contacting the receptor with a peptide, wherein the peptide comprises residues 24 to 37 of SEQ ID NO:2; and whereby the receptor binds the peptide. Within one embodiment of the method, the receptor is a GHS-R. Within a further embodiment of the method the receptor comprises residues 41 to 326 of SEQ ID NO:5. Within a further embodiment of the method, the receptor comprises residues 1 to 366 of SEQ ID NO:5. Within another embodiment of the method, the receptor is immobilized on a cell membrane.

Within another aspect, the invention provides a method of sorting cells comprising; immobilizing a peptide comprising residues 24 to 37 of SEQ ID NO:2 on a solid surface; contacting the peptide with cells expressing a receptor, whereby the peptide binds the receptor forming a peptide-receptor complex; washing the peptide-receptor complex with buffer to remove unbound receptor; dissociating the peptide-receptor complex; and recovering the purified receptor-expressing cells. Within an embodiment of the method, the receptor is a GHS-R. Within a further embodiment of the method, the receptor comprises residues 41 to 326 of SEQ ID NO:5.

Within another aspect of the invention is provided a method of purifying a peptide comprising; immobilizing cells expressing a receptor, wherein the receptor comprises residues 41 to 326 of SEQ ID NO:5; contacting the immobilized cells with solutions containing a peptide, wherein the peptide comprises residues 24 to 37 of SEQ ID NO:2; whereby the peptide binds the receptor forming a peptide-receptor complex; washing the peptide-receptor complex with buffer to remove unbound peptide; dissociating the peptide-receptor complex; and recovering the purified peptide.

Within another aspect the invention provides a method of stimulating signal transduction in a cell expressing a receptor comprising; providing an immobilized receptor; contacting the receptor with a peptide, wherein the peptide comprises residues 24 to 37 of SEQ ID NO:2; whereby the peptide and receptor form a peptide-receptor complex; and whereby a signal is transduced in the cell.

Within another aspect the invention provides a method of modulating the secretion of hormones in cells in vitro or in vivo comprising; administering a peptide comprising residues 24 to 37 of SEQ ID NO:2 to the cells; and forming a peptide-receptor complex with a receptor expressed by the cells.

Within another aspect, the invention provides a method of modulating neural development and/or utilization comprising: administering a peptide comprising residues 24 to 37 of SEQ ID NO:2 to a patient in need thereof; and forming a peptide-receptor complex.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985) (SEQ ID NO:x), substance P, Flag™ peptide (Hopp et al., *Biotechnology* 6:1204-1210, 1988), streptavidin binding peptide, maltose binding protein (Guan et al., *Gene* 67:21-30, 1987), cellulose binding protein, thioredoxin, ubiquitin, T7 polymerase, or other antigenic epitope or binding domain. See, in general, Ford et al., *Protein Expression and Purification* 2: 95-107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.).

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "ortholog" or "species homolog", denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "peptide-receptor complex" is formed when a peptide, or ligand, binds to a receptor resulting in a change in the properties of the receptor. This change can result in an initiation of a cascade of reactions leading to a change in cellular function, or the inability of the receptor to bind additional peptides. The forming of a peptide-receptor complex can be reversible.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain or multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is directed to a novel method of forming a peptide-receptor complex with a previously described secreted protein, zsig33 (Sheppard, P. O., WO98/42840:1998) and a receptor, GHS-R (Howard, A. D. et al., Science 273: 974-977, 1996). The present invention is also directed to a limited number of variants of said peptide and receptor. The discovery of this novel method of forming a peptide-receptor complex is important for further elucidation of the how the body maintains its nutritional homeostasis and development of therapeutics to intervene in those processes, as well as other uses that will be apparent from the teachings herein.

The present invention is based upon the identification of a previously described secreted polypeptide known as zsig33 (Sheppard, P. O., WO 98/42840) as the peptide ligand for an orphan receptor known as GHS-R (Feighner, S. D. et al., Science 284: 2184-2188, 1999). The zsig33 ligand has homology to motilin and has been found to be transcribed in the gastrointestinal system. The orphan receptor has homology to the motilin receptor, GPR38. Polynucleotide and polypeptide sequences for zsig33 are shown in SEQ ID NOs: 1 and 2, respectively. SEQ ID NO:3 is the degenerate polynucleotide sequence for SEQ ID NO:2. Polynucleotide and polypeptide sequences for the GHS-R orphan receptor are shown in SEQ ID NOs: 4 and 5, respectively. SEQ ID NO:6 is the degenerate polynucleotide sequence for SEQ ID NO:5. Polynucleotide and polypeptide sequences for motilin are shown in SEQ ID NOs: 7 and 8, respectively. The motilin receptor, GPR38 has two isoforms which result from alternate splicing events. See Feighner, F. D. supra. The polynucleotide and polypeptide sequences for the long form, GPR-38A, are shown in SEQ ID NOs:9, and 10, respectively. The polynucleotide and polypeptide sequences for the short form, GPR-38B, are shown in SEQ ID NOs: 11 and 12, respectively.

Motilin is member of a family of polypeptides that regulate the gastrointestinal physiology. The family of polypeptides important in gastrointestinal regulation to which motilin belongs includes glucagon, gastrin, galanin, and vasoactive intestinal peptide (VIP). These polypeptides are synthesized in a precursor form that requires multiple steps of processing to the active form. Particularly relevant to the peptide of the present invention are motilin, VIP and galanin, where processing involves removal of signal sequence, followed by cleavage of one or more accessory peptides to release the active peptide. The resulting active peptide is generally small (6-30 amino acids) and may require further post-translational modifications, such as amidation, sulfation or pyrrolidan carbonylic acid modification of glutamic residues.

A receptor belonging to the class of G protein-coupled receptors has been identified for motilin (Feighner, S. D. et al., supra). Two forms of the motilin receptor (GPR38-A, and GPR38-B) were shown resulting from alternative splicing events. Members of this receptor class appear to activate the phospholipase C signal transduction pathway.

Analysis of the tissue distribution of the mRNA corresponding to said secreted zsig33 protein showed that expression was highest in stomach, followed by apparent but decreased expression levels in small intestine and pancreas. The partial sequence for the secreted zsig33 protein was derived from a pancreatic library, and has also been shown in lung cDNA libraries. In vitro binding studies have shown that the zsig33 peptide binds to kidney, duodenum, and jejunum. (See Example 9.) Thus, binding of the zsig33 ligand to the GHS-R is expected in, but not limited to tissues such as stomach, small intestine, pancreas, lung, kidney, duodenum, jejunum, and brain.

An embodiment of the present invention is the binding of zsig33 polypeptide to a G protein-coupled receptor. GHS-R is a G protein-coupled receptor that has seven membrane-spanning hydrophobic regions which are thought to form seven transmembrane a helices. Thus the amino terminus of the polypeptide from residues 1 to 40 of SEQ ID NO:5 is extracellular. The first transmembrane a helix is formed by residues 41 to 66 of SEQ ID NO:5; the second transmembrane a helix is formed by residues 73 to 96 of SEQ ID NO:5; the third transmembrane a helix is formed by residues 118 to 139 of SEQ ID NO:5; the fourth transmembrane a helix is formed by residues 163 to 183 of SEQ ID NO:5; the fifth transmembrane a helix is formed by residues 212 to 235 of SEQ ID NO:5; the sixth transmembrane a helix is formed by residues 264 to 285 of SEQ ID NO:5; and the seventh transmembrane a helix is formed by residues 303 to 326 of SEQ ID NO:5. Thus portions of the polypeptide which are extracellular are residues 1 to 40 of SEQ ID NO:5; residues 97 to 117 of SEQ ID NO:5; residues 184 to 211 of SEQ ID NO:5; and residues 286 to 302 of SEQ ID NO:5. Portions of the polypeptide which are cytoplasmic are residues 67 to 72 of SEQ ID NO:5; residues 140 to 162 of SEQ ID NO:5; residues 236 to 263 of SEQ ID NO:5; and residues 327 to 366 of SEQ ID NO:5. A loop between a helices 5 and 6 (i.e., residues 236 to 263 of SEQ ID NO:5) as well as the C terminal segment (i.e., residues 327 to 366 of SEQ ID NO:5) face the cytosol and are important for interaction with the G protein. One skilled in the art will recognize that such boundaries are approximate and may vary by +/−4 amino acid residues. Additionally, post-translational disulfide bonds are expected between residues 116 and 198 of SEQ ID NO:5. Binding of the zsig33 ligand, or variant thereof, to the GHS-R causes the G protein to release its bound GDP and to bind GTP, thus, activating the G protein. In general, activated G proteins then bind to an affector enzyme which catalyzes the formation of a second messenger. In the case of the zsig33 ligand binding to the GHS-R the result of such second messenger can be measured by biological events such as, for example, gastric contractility, modulation of nutrient uptake, modulation of growth hormones, modulation of the secretion of digestive enzymes and hormones, and/or modulation of secretion of enzymes and/or hormones in the pancreas, as well as by other assays herein.

The release of growth hormone stimulates growth in many tissues and has effects on metabolic processes such as stimulating protein synthesis and free fatty acid mobilization as well as stimulating metabolism from a variety of energy sources from carbohydrates to fatty acids. Deficiency of growth hormone can result in medical disorders such as dwarfism.

Control of growth hormone release is under tight control either directly, or indirectly, by hormones and neurotransmitters. For example, growth hormone release is stimulated by growth hormone releasing hormone (GHRH) and inhibited by somatostatin, both of which are released by the hypothalamus and act primarily in the pituitary. Growth hormone release can also be stimulated by other compounds, such as, for example, L-3,4-dihydroxyphenylalanine, glucagon, vasopressin, pituitary adrenyl cyclase activating peptide (PACAP), muscarinic receptor agonists and synthetic peptides (i.e., growth hormone releasing peptide).

Growth hormone secretagogues are a class of small peptides which stimulate the release of growth hormone from pituitary cells by a mechanism of action other than that of GHRH, .i.e., by binding a different receptor (GHS-R) in the pituitary and hypothalalmus. Thus, the binding of this receptor can play a role in regulating growth hormone secretion in extraneuroendocrine activities, such as, for example, sleep and food intake. Therefore, the secretion of growth hormone can be regulated by the formation of a peptide-receptor complex between zsig33 and GHS-R.

One skilled in the art will recognize that the present invention includes variant polynucleotide sequences of both the ligand (zsig33) and the receptor (GHS-R). These variants are encompassed by conservative amino acids substitutions, allelic variants, and variants produced by degenerate polynucleotide sequences.

The active zsig33 peptides are predicted to result from a C-terminal cleavage after amino acid residue 37 (Gln) or residue 41 (Ser) of SEQ ID NO: 2. However, many of the gut-brain peptides require multiple cleavages. For example, progastrin peptide is 101 amino acids, and is cleaved at the N-terminus resulting in sequentially smaller peptides (G34, G17 and G14) (Sugano et al., *J. Biol. Chem.* 260:11724-11729, 1985). Other peptides that require multiple processing steps include glucagon, for which C-terminal cleavages result in glucagon-like peptide 1 and glucagon-like peptide 2 and galanin, in which processing involves cleavage of a C-terminal peptide known as GMAP. Therefore, a zsig33 peptide based on cleavage after amino acid 37 of SEQ ID NO: 2 (Gln) was synthesized and resulted in a 14 amino acid peptide with biological activity (from amino acid residue 24 (Gly) to amino acid residue 37 (Gln) of SEQ ID NO: 2). See Example 4.

Multiple signal peptidase cleavages are expected in the present invention. Thus, the amino terminal of the zsig33 peptides can begin with glycine, residue 24 of SEQ ID NO:2, serine, residues 25 or 26 of SEQ ID NO:2 or phenylalanine, residue 27 of SEQ ID NO:2.

Dibasic peptide sites are often necessary to generate bioactive molecules in the gut-hormone peptide family. Such sites are present at residues 38 and 39 (Arg-Lys) and residues 42 and 43 (Lys-Lys) of SEQ ID NO:2. Thus, a protease (i.e., a metalloprotease, serine protease, aspartic protease, or cysteine protease) important for the activation of zsig33 cleaves the zsig33 polypeptide after these dibasic sites resulting in peptides which terminate in residues 39 or 43 of SEQ ID NO:2. (Cleavages can also occur after monobasic amino acids or other sites as well.) Carboxy-peptidases are likely to remove one or more residues from the carboxyl terminal of the active peptides. Thus, the processing of the active peptides by proteases and carboxy-peptidases result in the active zsig33 peptides which terminate in residue 37 (Glu) or 41 (Ser) of SEQ ID NO:2.

Based on analysis of the motilin family, residues 27 to 32 of SEQ ID NO:2 will be essential for receptor binding and activation. (Miller, P. et al., *Peptides* 16(1):11-18, 1995; and Peeters, T. L. et al. *Peptides* 13(6):1103-1107, 1992). It should be noted that serine (residue 29 of SEQ ID NO:8, motilin) has been shown to be an isoleucine by Schubert, H. et al., *Can. J. Biochem.* 52:7-8, 1974. Furthermore, this analysis suggests that residues 27 (Phe), 28 (Leu), 29 (Ser) and 32 (His) of SEQ ID NO:2 are particularly important residues for receptor binding and/or activity. Substitutions of residues within this six residue peptide, can result in variants with altered affinity of the peptide for the receptor or altered activation of the receptor. Such alterations can result in agonistic as well as antagonistic activity.

Additional substitutions of residues of zsig33 peptides are further described herein. Conservative amino acid substitutions of certain residues between residues 27 (Phe) and residue 37 (Gln) of SEQ ID NO:2 result in variants which are potential antagonists. These variants will bind the receptor with high affinity, but cause low receptor activation. Preferably these positions are at residues 27 (Phe), 28 (Leu), 30 (Pro), and 32 (His) of SEQ ID NO:2.

Substitutions of residues in zsig33 peptides may also result in variants which are agonists. Such substitutions may be based on conservative amino acid substitutions as shown in Table 2, or based on predictions made by comparison to the active peptide of motilin, which are listed in Table A. These substitutions include positions 27 (Phe), 28 (Leu), and 32 (His) of SEQ ID NO:2. It is predicted, for example, that residue 27 (Phe) of SEQ ID NO:2 can be substituted with leucine, valine, or isoleucine; residue 28 (Leu) of SEQ ID NO:2 can be substituted with phenylalanine, valine, tyrosine or isoleucine; and that residue 32 (His) of SEQ ID NO:2 can be substituted with phenylalanine, or lysine. Similarly, residue 30 (Pro) of SEQ ID NO:2 can be substituted with alanine, glycine, isoleucine, valine, or leucine.

Additionally, there are positions of zsig33 peptides at which mutations are not predicted to result in alteration of the binding affinity or activation of the receptor upon binding these mutants. These positions include, for example, residue 29 (Ser) of SEQ ID NO:2, at which substitution with alanine, proline, threonine, or glycine is not predicted to alter the binding of the mutant, or variants, as compared to wild-type zsig33.

Miller, P. et al., ibid, suggests that residues 33 (Gly) and 34 (Glu) of motilin (SEQ ID NO:8) form a transition region, and that residues 35 (Leu) to 47 (Gln) of motilin (SEQ ID NO:8) form an alpha helix which stabilizes the interactions of the receptor binding portion of motilin (residues 26 to 32 of SEQ ID NO:8) to its receptor. Similarly, the helical region, residues 33 (Gln) to residue 41 (Ser) of zsig33 peptides (SEQ ID NO:2), can be substituted with residues that maintain the hydrophobic, hydrophilic and electrostatic nature required for forming a helix. These substitutions include, glutamine, asparagine, serine, threonine, histidine, alanine, glutamic acid, aspartic acid, lysine, and arginine for positions 33 (Gln), 34 (Arg), 36 (Gln), 37 (Gln), 38 (Arg), 39 (Lys), 40 (Glu), and 41 (Ser) of SEQ ID NO:2 and methionine, leucine, valine, isoleucine, tryptophan, and phenylalanine for position 35 (Val) of SEQ ID NO:2. These substitutions will maintain the helical conformation and presentation of the binding site of the ligand to the receptor. Zsig33 peptides can be produced by in vitro or in vivo expression as well as chemical synthesis.

Critical carboxyl-terminal residues of motilin have been identified by Feighner, S. D. et al., ibid. If motilin is truncated with these residues, there is a sharp decrease in receptor binding and activity. These positions are residues 36 (Gln), and residue 37 (Arg) of motilin as shown in SEQ ID NO:8. An analysis of the amino acid sequence of zsig33 peptides shows that residues 33 (Gln) and 34 (Arg) of SEQ ID NO:2 correspond to residues 36 and 37 of motilin, SEQ ID NO:8. Thus, zsig33 peptides may have conservative amino acid substitutions at these positions. These specific substitutions are listed in Table A.

Binding studies have suggested that motilin binds to two populations of receptors with varying affinities (Poitras, P., Peptides 17:701-707, 1996) suggesting that there are two forms of motilin binding these receptors. One such receptor is located in the neural cells of the antrum, and the second receptor is located in the smooth muscle cells of the duodenum. Similarly, there may be more than one receptor which binds the zsig33 peptide, or variants thereof, and the binding affinities may vary. Thus, the binding of zsig33 peptide to its receptor(s) may result in different and varying biological events depending on the receptor variant to which it binds.

A complete list of the variant zsig33 ligands contemplated by the present invention can be derived from the peptide substitutions listed in Table A, below.

TABLE A

Peptide Substitutions

| Position in SEQ ID NO: 2 | Wild-Type Residue | Substitutions: |
|---|---|---|
| 24 | Gly | Ser, Ala, Thr, Met |
| 25 | Ser | Gly, Ala, Thr, Met |
| 26 | Ser | Gly, Ala, Thr, Met |
| 27 | Phe | Trp, Tyr, Leu, Val, Ile |
| 28 | Leu | Ile, Val, Phe, Tyr |
| 29 | Ser | Gly, Ala, Thr, Met, Pro |

TABLE A-continued

Peptide Substitutions

| Position in SEQ ID NO: 2 | Wild-Type Residue | Substitutions: |
|---|---|---|
| 30 | Pro | Ala, Gly, Ile, Leu, Val |
| 31 | Glu | Asp |
| 32 | His | Arg, Lys, Phe, Tyr |
| 33 | Gln | Asn, Ser, Thr, His, Ala, Glu, Asp, Lys, Arg |
| 34 | Arg | Gln, Asn, Ser, Thr, His, Ala, Glu, Asp, Lys, |
| 35 | Val | Met, Leu, Ile, Trp, Phe |
| 36 | Gln | Asn, Ser, Thr, His, Ala, Glu, Asp, Lys, Arg |
| 37 | Gln | Asn, Ser, Thr, His, Ala, Glu, Asp, Lys, Arg |
| 38 | Arg | Asn, Ser, Thr, His, Ala, Glu, Asp, Lys, Gln |
| 39 | Lys | Asn, Ser, Thr, His, Ala, Glu, Asp, Gln, Arg |
| 40 | Glu | Asn, Ser, Thr, His, Ala, Gln, Asp, Lys, Arg |
| 41 | Ser | Asn, Gln, Thr, His, Ala, Glu, Asp, Lys, Arg |

The present invention provides polynucleotide molecules, including DNA and RNA molecules, that encode the zsig33 and GHS-R polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zsig33 polypeptide of SEQ ID NO:2. SEQ ID NO:6 is a degenerate DNA sequence that encompasses all DNAs that encode the GHS-R polypeptide of SEQ ID NO:5. Those skilled in the art will recognize that the degenerate sequence of SEQ ID NOs:3 and 6 also provides all RNA sequences encoding SEQ ID NOs:2 and 5 by substituting U for T. Thus, zsig33 polypeptide-encoding polynucleotides comprising nucleotide 1 to nucleotide 351 of SEQ ID NO:3, and comprising nucleotide 1 to nucleotide 1098 of SEQ ID NO:6, and their RNA equivalents are contemplated by the present invention. Table 1 sets forth the one-letter codes used within SEQ ID NOs:3 and 6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:3 and 6, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NOs:2 and 5. Variant sequences can be readily tested for functionality as described herein.

One of ordinary skill in the art will also appreciate that different species can exhibit "preferential codon usage." Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NOs:3 and 6 serve as templates for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NOs:1 and 3, or SEQ ID NOs:4 and 6, or a sequence complementary thereto under stringent conditions. Polynucleotide hybridization is well known in the art and widely used for many applications, see for example, Sambrook et al., *Molecular Cloning: A Laboratory Manual*, Second Edition, Cold Spring Harbor, N.Y., 1989; Ausubel et al., eds., *Current Protocols in Molecular Biology*, John Wiley and Sons, Inc., NY, 1987; Berger and Kimmel, eds., Guide to Molecular Cloning Techniques, *Methods in Enzymology*, volume 152, 1987 and Wetmur, *Crit. Rev. Biochem. Mol. Biol.* 26:227-59, 1990. Polynucleotide hybridization exploits the ability of single stranded complementary sequences to form a double helix hybrid. Such hybrids include DNA-DNA, RNA-RNA and DNA-RNA.

As an illustration, a nucleic acid molecule encoding a variant GHS-R polypeptide can be hybridized with a nucleic acid molecule having the nucleotide sequence of SEQ ID NOs:4 or 6 (or their complements) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., ExpressHyb™ Hybridization Solution from CLONTECH Laboratories, Inc., Palo Alto, Calif.) according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant GHS-R polypeptide hybridize with a nucleic acid molecule having the nucleotide sequences of SEQ ID NOs:4 or 6 (or their complements) under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

The present invention also contemplates GHS-R variant nucleic acid molecules that can be identified using two criteria: a determination of the similarity between the encoded polypeptides with the amino acid sequence of SEQ ID NO:5 (as described below), and a hybridization assay, as described above. Such GHS-R variants include nucleic acid molecules (1) that hybridize with a nucleic acid molecule having the nucleotide sequence of SEQ ID NOs:4 or 6 (or their complements) under stringent washing conditions, in which the wash stringency is equivalent to 0.5×-2×SSC with 0.1% SDS at 55-65° C., and (2) that encode a polypeptide having at least 80%, preferably 90%, more preferably, 95% or greater than 95% sequence identity to the amino acid sequence of SEQ ID NO:5. Alternatively, GHS-R variants can be characterized as nucleic acid molecules (1) that hybridize with a nucleic acid molecule having the nucleotide sequence of SEQ ID NOs:4 or 6 (or their complements) under highly stringent washing conditions, in which the wash stringency is equivalent to 0.1×-0.2×SSC with 0.1% SDS at 50-65° C., and (2) that encode a polypeptide having at least 80%, preferably 90%, more preferably 95% or greater than 95% sequence identity to the amino acid sequence of SEQ ID NO:5.

Regions of conserved amino acids of the GHS-R can be used as a tool to identify new family members. These regions are residues 275 to 280 of SEQ ID NO:5; residues 319 to 324 of SEQ ID NO:5; residues 139 to 144 of SEQ ID NO:5; residues 124 to 129 of SEQ ID NO:5; and residues 302 to 307 of SEQ ID NO:5. One skilled in the art is able to determine the degenerate nucleotide and the complement of the degenerate nucleotide sequences these purposes. For instance, reverse transcription-polymerase chain reaction (RT-PCR) can be used to amplify sequences encoding the conserved regions from RNA obtained from a variety of tissue sources or cell lines. In particular, highly degenerate primers designed from the GHS-R sequences are useful for this purpose.

As previously noted, the isolated polynucleotides of the present invention include DNA and RNA. Methods for preparing DNA and RNA are well known in the art. In general, RNA is isolated from a tissue or cell that produces large amounts of zsig33 or GHS-R RNA. Such tissues and cells are identified by Northern blotting (Thomas, *Proc. Natl. Acad. Sci. USA* 77:5201, 1980), and include stomach, small intestine, and pancreas, for zsig33 peptides, and pituitary, hypothalamus, hippocampus and central nervous system for GHS-R.

Total RNA can be prepared using guanidine isothiocyante extraction followed by isolation by centrifugation in a CsCl gradient (Chirgwin et al., *Biochemistry* 18:52-94, 1979). Poly $(A)^+$ RNA is prepared from total RNA using the method of Aviv and Leder (*Proc. Natl. Acad. Sci. USA* 69:1408-12, 1972). Complementary DNA (cDNA) is prepared from poly $(A)^+$ RNA using known methods. In the alternative, genomic DNA can be isolated. Polynucleotides encoding GHS-R polypeptides are then identified and isolated by, for example, hybridization or PCR.

Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to GHS-R, or other specific binding partners.

GHS-R polynucleotide or zsig33 polynucleotide sequences disclosed herein can also be used as probes or primers to clone 5' non-coding regions of a GHS-R or zsig33 gene, respectively. Promoter elements from a GHS-R or zsig33 gene could thus be used to direct the tissue-specific expression of heterologous genes in, for example, transgenic animals or patients treated with gene therapy. Cloning of 5' flanking sequences also facilitates production of GHS-R or zsig33 proteins by "gene activation" as disclosed in U.S. Pat. No. 5,641,670. Briefly, expression of an endogenous GHS-R or zsig33 gene in a cell is altered by introducing into the GHS-R or zsig33 locus a DNA construct comprising at least a targeting sequence, a regulatory sequence, an exon, and an unpaired splice donor site. The targeting sequence is a GHS-R 5' or zsig33 non-coding sequence that permits homologous recombination of the construct with the endogenous GHS-R or zsig33 locus, whereby the sequences within the construct become operably linked with the endogenous GHS-R or zsig33 coding sequence. In this way, an endogenous GHS-R or zsig33 promoter can be replaced or supplemented with other regulatory sequences to provide enhanced, tissue-specific, or otherwise regulated expression.

The polynucleotides of the present invention can also be synthesized using DNA synthesizers. For example, the phosphoramidite method can be used. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick and Pasternak, *Molecular Biotechnology, Principles and Applications of Recombinant DNA*, (ASM Press, Washington, D.C. 1994); Itakura et al., *Annu. Rev. Biochem.* 53: 323-356 (1984) and Climie et al., *Proc. Natl. Acad. Sci. USA* 87:633-7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are GHS-R polypeptides from other mammalian species, including murine, porcine, ovine, bovine, canine, feline, equine, and other primate polypeptides. Orthologs of human GHS-R can be cloned using information and compositions provided by the present invention in combination with conventional cloning techniques. For example, a cDNA can be cloned using mRNA obtained from a tissue or cell type that expresses GHS-R as disclosed herein. Suitable sources of mRNA can be identified by probing Northern blots with probes designed from the sequences disclosed herein. A library is then prepared from mRNA of a positive tissue or cell line. A GHS-R-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human GHS-R sequences disclosed herein. Within an additional method, the cDNA library can be used to transform or transfect host cells, and expression of the cDNA of interest can be detected with an antibody to a GHS-R polypeptide. Similar techniques can also be applied to the isolation of genomic clones.

Those skilled in the art will recognize that the sequences disclosed in SEQ ID NOs:4 and 6 represent a single allele of human GHS-R and that allelic variation and alternative splicing are expected to occur. Allelic variants of this sequence can be cloned by probing cDNA or genomic libraries from different individuals according to standard procedures. Allelic variants of the DNA sequences shown in SEQ ID NOs:4 and 6, including those containing silent mutations and those in which mutations result in amino acid sequence changes, are within the scope of the present invention, as are proteins which are allelic variants of SEQ ID NO:5. cDNAs generated from alternatively spliced mRNAs, which retain the properties of the GHS-R polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated GHS-R polypeptides that are substantially similar to the polypeptides of SEQ ID NO:5 and their orthologs. Such polypeptides will more preferably be at least 90% identical, and more preferably 95% or more identical to SEQ ID NO:5 and its orthologs. Percent sequence identity is determined by conventional methods. See, for example, Altschul et al., *Bull. Math. Bio.* 48: 603-16, 1986 and Henikoff and Henikoff, *Proc. Natl. Acad. Sci. USA* 89:10915-9, 1992. Briefly, two amino acid sequences are aligned to optimize the alignment scores using a gap opening penalty of 10, a gap extension penalty of 1, and the "blosum 62" scoring matrix of Henikoff and Henikoff (*ibid.*) as shown in Table 3 (amino acids are indicated by the standard one-letter codes). The percent identity is then calculated as:

$$\left[ \frac{\text{Total number of identical matches}}{\begin{array}{c}\text{length of the longer sequence plus the}\\ \text{number of gaps introduced into the longer}\\ \text{sequence in order to align the two sequences}\end{array}} \right] \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant GHS-R. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:5) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably 3, with all other parameters set at default.

The present invention includes nucleic acid molecules that encode a polypeptide having one or more conservative amino acid changes, compared with the amino acid sequence of SEQ ID NO:5. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in a GHS-R gene can be introduced by substituting nucleotides for the nucleotides recited in SEQ ID NO:4. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). The ability of such variants to promote cell-cell interactions can be determined using a standard method, such as the assay described herein. Alternatively, a variant GHS-R polypeptide can be identified by the ability to specifically bind anti-GHS-R antibodies.

Essential amino acids in the polypeptides of the present invention can be identified according to procedures known in the art, such as site-directed mutagenesis or alanine-scanning mutagenesis (Cunningham and Wells, *Science* 244: 1081-5, 1989; Bass et al., *Proc. Natl. Acad. Sci. USA* 88:4498-502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699-708, 1996. Sites of zsig33-GHS-R biding, can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-12, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related G protein-coupled receptors.

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed GHS-R DNA and polypeptide sequences can be generated through DNA shuffling, as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., gastric contractility, modulation of nutrient uptake, modulation of growth hormones, modulation of the secretion of digestive enzymes and hormones, and/or modulation of secretion of enzymes and/or hormones in the pancreas) can be recovered from the host cells and rapidly sequenced using modern equipment. These methods allow the rapid determination of the importance of individual amino acid residues in a polypeptide of interest, and can be applied to polypeptides of unknown structure.

Regardless of the particular nucleotide sequence of a variant GHS-R gene, the gene encodes a polypeptide that is characterized by its ability to bind specifically to the zsig33 ligand or an anti-GHS-R antibody. More specifically, variant GHS-R genes encode polypeptides which exhibit at least 50%, and preferably, greater than 70, 80, or 90%, of the activity of polypeptide encoded by the human GHS-R gene described herein.

Variant GHS-R polypeptides or substantially homologous GHS-R polypeptides are characterized as having one or more amino acid substitutions, deletions or additions. These changes are preferably of a minor nature, that is conservative amino acid substitutions and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from 366 to 1800 amino acid residues that comprise a sequence that is at least 85%, preferably at least 90%, and more preferably 95% or more identical to the corresponding region of SEQ ID NO:5. Polypeptides comprising affinity tags can further comprise a proteolytic cleavage site between the GHS-R polypeptide and the affinity tag. Preferred such sites include thrombin cleavage sites and factor Xa cleavage sites.

For any GHS-R polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise GHS-R variants based upon the nucleotide and amino acid sequences described herein. Accordingly, the present invention includes a computer-readable medium encoded with a data structure that provides at least one of the following sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The present invention further provides a variety of other polypeptide fusions and related multimeric proteins comprising one or more polypeptide fusions. For example, G-protein coupled receptors can be prepared as a fusion to a dimerizing protein, as disclosed in U.S. Pat. Nos. 5,155,027 and 5,567,584. Preferred dimerizing proteins in this regard include other G protein-coupled receptors, G protein-coupled receptor fragments, or polypeptides comprising other members of the G protein-coupled receptor family of proteins, such as, for example, GPR38 (i.e., GPR38A or GPR38B, the motilin receptor) as well as Ig-Hepta. See also, Abe, J. et al., *J Biol Chem*, Vol. 274:19957-19964, 1999. These domain fusions, or domain fragment fusions, or fusions with other G protein-coupled receptor peptides can be expressed in genetically engineered cells to produce a variety of multimeric G protein-linked receptor-like analogs.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between GHS-R of the present invention with the functionally equivalent domain(s) from another family member, such as GPR38. Such domains include, but are not limited to, conserved motifs such as the secretory signal sequence, transmembrane spanning domains, and signaling domains. Such fusion proteins would be expected to have a biological functional profile that is the same or similar to polypeptides of the present invention or other known G protein-coupled receptor-like family proteins (e.g. GPR38), depending on the fusion constructed. Moreover, such fusion proteins may exhibit other properties as disclosed herein.

Moreover, using methods described in the art, polypeptide fusions, or hybrid GHS-R proteins, are constructed using regions or domains of the inventive GHS-R in combination with those of other G protein-coupled receptors (e.g. GPR38), with members of other receptor families, such as, for example, the b-adrenergic receptor family, or with other heterologous proteins (Sambrook et al., *ibid.*, Altschul et al., *ibid.*, Picard, *Cur. Opin. Biology,* 5:511-5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Auxiliary domains can be fused to zsig33 polypeptides to target them to specific cells, tissues, or macromolecules as identified in Example 9, herein. For example, a protease, or protease fragment, could be targeted to a predetermined cell type by fusing it to a zsig33 polypeptide domain or fragment that specifically binds to a GHS-R polypeptide on the surface of the target cell. In this way, polypeptides, polypeptide fragments and proteins can be targeted for therapeutic or diagnostic purposes. Such zsig33 polypeptide domains or fragments can be fused to two or more moieties, such as an affinity tag for purification and a targeting-GHS-R. Polypeptide fusions can also comprise one or more cleavage sites, particularly between domains. See, Tuan et al., *Connective Tissue Research* 34:1-9, 1996.

Polypeptide fusions of the present invention will generally contain not more than about 1,500 amino acid residues, preferably not more than about 1,200 residues, more preferably not more than about 1,000 residues, and will in many cases be considerably smaller. For example, residues of zsig33 or GHS-R polypeptides can be fused to *E. coli* b-galactosidase (1,021 residues; see Casadaban et al., *J. Bacteriol.* 143:971-980, 1980), a 10-residue spacer, and a 4-residue factor Xa cleavage site. In a second example, residues of zsig33 or GHS-R polypeptide can be fused to maltose binding protein (approximately 370 residues), a 4-residue cleavage site, and a 6-residue polyhistidine tag.

To direct the export of either a zsig33 or GHS-R polypeptide from the host cell, the zsig33 DNA is linked to a second DNA segment encoding a secretory peptide, such as a t-PA secretory peptide or a secretory peptide derived from zsig33 or GHS-R secretory peptide. To facilitate purification of the secreted polypeptide(s), a C-terminal extension, such as a poly-histidine tag, substance P, Flag peptide (Hopp et al., *Bio/Technology* 6:1204-1210, 1988; available from Eastman Kodak Co., New Haven, Conn.), maltose binding protein, or another polypeptide or protein for which an antibody or other specific binding agent is available, can be fused to the zsig33 or GHS-R polypeptide.

The present invention also includes "functional fragments" of zsig33 and GHS-R polypeptides and nucleic acid molecules encoding such functional fragments. Routine deletion analyses of nucleic acid molecules can be performed to obtain functional fragments of a nucleic acid molecule that encodes a zsig33 or GHS-R polypeptide. As an illustration, DNA molecules having the nucleotide sequence of SEQ ID NOs:1 or 3, or SEQ ID NOs:4 or 6 can be digested with Bal31 nuclease to obtain a series of nested deletions. The fragments are then inserted into expression vectors in proper reading frame, and the expressed polypeptides are isolated and tested for cell-cell interactions, or for the ability to bind anti-zsig33 or anti-GHS-R antibodies. One alternative to exonuclease digestion is to use oligonucleotide-directed mutagenesis to introduce deletions or stop codons to specify production of a desired fragment. Alternatively, particular fragments of an zsig33 or GHS-R gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems,* Cantell (ed.), pages 65-72 (Nijhoff 1987), Herschman, "The EGF Receptor," in *Control of Animal Cell Proliferation,* Vol. 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of zsig33 or GHS-R gene that have amino acid changes, compared with the amino acid sequence of SEQ ID NOs:2 or 5, respectively. A variant zsig33 gene can be identified on the basis of structure by determining the level of identity with nucleotide and amino acid sequences of SEQ ID NOs:1, or 2, as discussed above, as well as by a comparison with Table A, herein. A variant GHS-R gene can be identified on the basis of structure by determining the level of identity with nucleotide and amino acid sequences of SEQ ID NOs:4, or 5, as discussed above. An alternative approach to identifying a variant gene on the basis of structure is to determine whether a nucleic acid molecule encoding a potential variant zsig33 or GHS-R gene can hybridize to a nucleic acid molecule having the nucleotide sequence of SEQ ID NOs:1 and 3, or SEQ ID NOs:4 and 6, as discussed above.

Using the methods discussed herein, one of ordinary skill in the art can identify and/or prepare a variety of polypeptide fragments or variants of SEQ ID NO:5 or that retain the activity of the wild-type GHS-R protein. Such polypeptides may include additional amino acids from, for example, a secretory domain, part or all of a transmembrane and intracellular domains, including amino acids responsible for intracellular signaling; fusion domains; affinity tags; and the like.

The present invention also provides polypeptide fragments or peptides comprising an epitope-bearing portion of zsig33 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides contain at least four to ten amino acids, preferably at least ten to fifteen amino acids, more preferably 15 to 30 amino acids of SEQ ID NOs:2 or 5. Such epitope-bearing peptides and polypeptides can be produced by fragmenting a zsig33 or GHS-R polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

As an illustration, potential antigenic sites in zsig33 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The results of this analysis indicated that a peptide consisting of amino acid residues 30 to 50 of SEQ ID NO:2; residues 57 to 73 of SEQ ID NO:2; and residues 109 to 117 of SEQ ID NO:2 are antigenic peptides.

Zsig33 polypeptides can also be used to prepare antibodies that bind to zsig33 epitopes, peptides or polypeptides. The zsig33 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a zsig33 polypeptide (e.g., SEQ ID NO:2). Polypeptides comprising a larger portion of a zsig33 polypeptide, i.e., from 10 to 30 residues, up to the entire length of the amino acid sequence are included. Antigens or immunogenic epitopes can also include attached tags, adjuvants and carriers, as described herein. Suitable antigens include the zsig33 polypeptides encoded by SEQ ID NO:2 from amino acid number 24 to amino acid number 117, or a contiguous 9 to 94 amino acid fragment thereof. Other suitable antigens include residue 1 to residue 23, of SEQ ID NO:2; residue 24 to residue 37 of SEQ ID NO:2; residue 24 to 41 of SEQ ID NO:2; residue 24 to 117 of SEQ ID NO:2; and residue 42 to 117 of SEQ ID NO:2. Preferred peptides to use as antigens are hydrophilic peptides such as those predicted by one of skill in the art from a hydrophobicity plot. GHS-R hydrophilic peptides include peptides comprising amino acid sequences selected from the group consisting of: residues 28 to 49 of SEQ ID NO:2; residues 57 to 75 of SEQ ID NO:2; residues 89 to 97 of SEQ ID NO:2; and residues 107 to 117 of SEQ ID NO:2; or a contiguous 9 to 94 amino acid fragment containing a portion of any one of these peptides. Additionally, sequences of amino acids which are presented on the surface of a folded protein will be antigenic. For zsig33 peptides, suitable surface presenting peptides include peptides comprising amino acids selected from the group consisting of: residues 27 to 52 of SEQ ID NO:2; residues 56 to 79 of SEQ ID NO:2; residues 87 to 98 of SEQ ID NO:2; and residues 105 to 117 of SEQ ID NO:2. Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual*, Second Edition, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zsig33 polypeptide or a fragment thereof. The immunogenicity of a zsig33 polypeptide may be increased through the use of an adjuvant, such as alum (aluminum hydroxide) or Freund's complete or incomplete adjuvant. Polypeptides useful for immunization also include fusion polypeptides, such as fusions of zsig33 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Alternative techniques for generating or selecting antibodies useful herein include in vitro exposure of lymphocytes to zsig33 protein or peptide, and selection of antibody display libraries in phage or similar vectors (for instance, through use of immobilized or labeled zsig33 protein or peptide). Genes encoding polypeptides having potential zsig33 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from CLONTECH Laboratories, Inc., (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the GHS-R sequences disclosed herein to identify proteins which bind to GHS-R. These "binding proteins", which include zsig33, interact with GHS-R polypeptides and can be used for tagging cells and for isolating homolog polypeptides by affinity purification. They can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zsig33 "antagonists" to block zsig33 binding and signal transduction in vitro and in vivo. These anti-zsig33 binding proteins would be useful for modulating, for example, platelet aggregation, apoptosis, neurogenesis, myogenesis, immunologic recognition, tumor formation, and cell-cell interactions in general.

Antibodies are determined to be specifically binding if they exhibit a threshold level of binding activity (to a zsig33 polypeptide, peptide or epitope) of at least 10-fold greater than the binding affinity to a control (non-zsig33) polypeptide. The binding affinity of an antibody can be readily determined by one of ordinary skill in the art, for example, by Scatchard analysis (Scatchard, G., *Ann. NY Acad. Sci.* 51: 660-672, 1949).

A variety of assays known to those skilled in the art can be utilized to detect antibodies which specifically bind to zsig33 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. Antibodies can also be screened for binding to wild-type versus mutant zsig33 protein or polypeptide. Additionally, antibodies to the zsig33/GSH-R complex can also be identified.

Antibodies to zsig33 may be used for tagging cells that express zsig33; for isolating zsig33 by affinity purification; for diagnostic assays for determining circulating levels of zsig33 polypeptides; for detecting or quantitating soluble zsig33 as marker of underlying pathology or disease; in analytical methods employing FACS; for screening expression libraries; for generating anti-idiotypic antibodies; as neutralizing antibodies or as antagonists to block the binding of zsig33 to GHS-R in vitro and in vivo; and to detect the zsig33/GHS-R complex formed by the binding of zsig33 to GSH-R. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zsig33 or fragments thereof may be used in vitro to detect denatured zsig33 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (GHS-R, for instance). More specifically, zsig33 polypeptides or anti-zsig33 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, a fusion protein including only a peptide comprising residues 24 to 41 os SEQ ID NO:2 may be suitable for directing a detectable molecule, a cytotoxic molecule or a complementary molecule to a cell or tissue type of interest, such as, for example, pituitary, hypothalamus, hippocampus, and central nervous system, in general.

In another embodiment, zsig33-cytokine fusion proteins or antibody-cytokine fusion proteins can be used for enhancing in vivo killing of target tissues (for example, stomach, kidney, jejunum, duodenum, pancreas, small intestine, and lung), if the zsig33 polypeptide or anti-zsig33 antibody targets hyperproliferative tissues from these organs. (See, generally, Hornick et al., *Blood* 89:4437-47, 1997). Hornick, et al., described fusion proteins that enable targeting of a cytokine to a desired site of action, thereby providing an elevated local concentration of cytokine. Suitable zsig33 polypeptides or anti-zsig33 antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

In yet another embodiment, if the zsig33 polypeptide or anti-zsig33 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy.

The bioactive polypeptide or antibody conjugates described herein can be delivered intravenously, intraarterially or intraductally, or may be introduced locally at the intended site of action.

The zsig33 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zsig33 or GHS-R polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig33 or GHS-R polypeptide into the secretory pathway of a host cell, a secretory signal sequence (also known as a leader sequence, prepro sequence or pre sequence) is provided in the expression vector. The secretory signal sequence may be that of zsig33, GHS-R, or may be derived from another secreted protein (e.g., t-PA) or synthesized de novo. The secretory signal sequence is operably linked to the zsig33 or GHS-R DNA sequence, i.e., the secretory signal sequence and the zsig33 (or GHS-R) sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

The native secretory signal sequence of the polypeptides of the present invention is used to direct other polypeptides into the secretory pathway. The present invention provides for such fusion polypeptides. A signal fusion polypeptide can be made wherein a secretory signal sequence derived from a zsig33 polypeptide (i.e., residues 1 to 23 of SEQ ID NO:2) is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Similarly, some of the a-helical, transmembrane-spanning domains of GHS-R can be substituted by a heterologous sequence providing different a-helical transmembrane domains from other G protein-linked receptors, or from, for example, members of the b adrenergic receptor family.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-5, 1982), DEAE-dextran mediated transfection (Ausubel et al., *ibid.*), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins, such as CD4, CD8, Class I MHC, or placental alkaline phosphatase, may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zsig33 baculovirus utilizes a transposon-based system described by Luckow (Luckow, V. A, et al., *J Virol* 67:4566-79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zsig33 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zsig33 or GHS-R. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971-6, 1990; Bonning, B. C. et al., *J. Gen. Virol.* 75:1551-6, 1994; and, Chazenbalk, G. D., and Rapoport, B., *J. Biol Chem* 270:1543-9, 1995. In such transfer vector constructs, a short or long version of the basic protein promoter can be used. Moreover, transfer vectors can be constructed which replace the native zsig33 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zsig33 secretory signal sequence. In addition, transfer vectors can include an in-frame fusion with DNA encoding an epitope tag at the C- or N-terminus of the expressed zsig33 polypeptide, for example, a Glu-Glu epitope tag (Grussenmeyer, T. et al., *Proc. Natl. Acad. Sci.* 82:7952-4, 1985). Using a technique known in the art, a transfer vector containing zsig33 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zsig33 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. Procedures used are generally described in available laboratory manuals (King, L. A. and Possee, R. D., *ibid.*; O'Reilly, D. R. et al., *ibid.*; Richardson, C. D., *ibid.*). Subsequent purification of the zsig33 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459-65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. The use of *Pichia methanolica* as host for the production of recombinant proteins is disclosed in U.S. Pat. Nos. 5,716,808, 5,736,383, 5,854,039, and 5,888,768.

Prokaryotic host cells, including strains of the bacteria *Escherichia coli*, *Bacillus* and other genera are also useful host cells within the present invention. Techniques for transforming these hosts and expressing foreign DNA sequences cloned therein are well known in the art (see, e.g., Sambrook et al., *ibid.*). When expressing a zsig33, or GHS-R, polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Within one aspect of the present invention, a GHS-R receptor (including transmembrane and intracellular domains) is produced by a cultured cell, and the cell is used to screen for variants of zsig33 ligand, including the natural ligand, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Generally, host cell(s) and receptor(s) from the same species are used. However cell lines can be engineered to express multiple receptor subunits from any species, thereby overcoming potential limitations arising from species specificity. In the alternative, species homologs of the human receptor cDNA can be cloned and used within cell lines from the same species, such as a mouse cDNA in the BaF3 cell line. Cell lines that are dependent upon one hematopoietic growth factor, such as IL-3, can thus be engineered to become dependent upon a zsig33 ligand.

Cells expressing functional GHS-R are used within screening assays. A variety of suitable assays are known in the art. These assays are based on the detection of a biological response in the target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of Alymar Blue™ (AccuMed, Chicago, Ill.) or 3-(4,5-dimethylthiazol-2-yl)-2,5-diphenyl tetrazolium bromide (MTT) (Mosman, *J. Immunol. Meth.* 65: 55-63, 1983). Alternative assays are also listed herein.

Another assay uses phospholipase C signal transduction to measure receptor binding. An exemplary assay of this sort measures release of $Ca^{2+}$ with aequorin, a bioluminescent $Ca^{2+}$-sensitive reporter protein. This assay is further described by Feighner, S. D. et al., supra. Hence, zsig33 peptides can be tested using an assay that measures phospholipase C transduction.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tent-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for zsig33 or GHS-R amino acid residues.

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zsig33 and GHS-R proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Proteins comprising a glu-glu tag can be purified by immunoaffinity chromatography according to conventional procedures. See, for example, Grussenmeyer et al., *ibid*. Maltose binding protein fusions are purified on an amylose column according to methods known in the art.

The polypeptides of the present invention can be isolated by a combination of procedures including, but not limited to, anion and cation exchange chromatography, size exclusion, and affinity chromatography. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529-39). Within additional embodiments of the invention, a fusion of the polypeptide of interest and an affinity tag (e.g., maltose-binding protein, an immunoglobulin domain) may be constructed to facilitate purification.

Zsig33 and GHS-R polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, zsig33 and GHS-R proteins can be prepared as monomers or multimers; glycosylated or non-glycosylated; pegylated or non-pegylated; and may or may not include an initial methionine amino acid residue.

The binding of GHS-R polypeptides to zsig33 polypeptides can be measured using a variety of assays that measure, for example, cell-cell interactions; ligand-receptor binding, and other biological functions associated with gut-hormone family members. Of particular interest is a change in gastrointestinal contractility, modulation of growth hormones, weight maintenance, and glucose absorption. Assays measuring ligand binding and gastrointestinal contractility are known in the art, and further described in the examples, herein. Additional assays for measuring growth hormone secretion, receptor binding, and body weight are described in Hansen, B. S. et al., *Eur. J. Endocrinol.* 141:180-189, 1999.

Proteins, including peptides resulting from alternative splicing, of the present invention are useful for modulation of gastrointestinal contractility, modulation of nutrient uptake, modulation of growth hormones, modulation of the secretion of digestive enzymes and hormones, and/or modulation of secretion of enzymes and/or hormones in the pancreas, and gastric reflux either working in isolation, or in conjunction with other molecules (growth factors, cytokines, etc.) in tissues such as stomach, duodenum, jejunum, kidney, small intestine, skeletal muscle, lung, pituitary, hypothalamus, hippocampus, and central nervous system, in general. Alternative splicing of zsig33 mRNA may be cell-type specific and confer activity to specific tissues.

Another assay of interest measures or detects changes in proliferation, differentiation, development and/or electrical coupling of muscle cells or myocytes. Additionally, the effects of a zsig33 polypeptides on cell-cell interactions of fibroblasts, myoblasts, nerve cells, white blood cells, immune cells, and tumor cells would be of interest to measure. Yet other assays examine changes in contractility, and secretion of hormones and enzymes.

The effects of zsig33 polypeptide, its antagonists and agonists, on tissue contractility can be measured in vitro using a tensiometer with or without electrical field stimulation. Such assays are known in the art and can be applied to tissue samples, such as gastrointestinal and other contractile tissue samples, and can be used to determine whether zsig33 polypeptide, its agonists or antagonists, enhance or depress contractility. Molecules of the present invention are hence useful for treating dysfunction associated with contractile tissues or can be used to suppress or enhance contractility in vivo. As such, molecules of the present invention have utility in treating gastrointestinal and growth related diseases.

The effect of the zsig33 polypeptides, antagonists and agonists of the present invention on contractility of tissues including gastrointestinal tissues can be measured in a tensiometer that measures contractility and relaxation in tissues. See, Dainty et al., *J. Pharmacol.* 100:767, 1990; Rhee et al., *Neurotox.* 16: 179, 1995; Anderson, M. B., *Endocrinol.* 114: 364-368, 1984; and Downing, S. J. and Sherwood, O. D, *Endocrinol.* 116:1206-1214, 1985. For example, measuring vasodilatation of aortic rings is well known in the art. Briefly, aortic rings are taken from 4 month old Sprague Dawley rats and placed in a buffer solution, such as modified Krebs solution (118.5 mM NaCl, 4.6 mM KCl, 1.2 mM $MgSO_4.7H_2O$, 1.2 mM $KH_2PO_4$, 2.5 mM $CaCl_2.2H_2O$, 24.8 mM $NaHCO_3$ and 10 mM glucose). One of skill in the art would recognize that this method can be used with other animals, such as rabbits, other rat strains, Guinea pigs, and the like. The rings are then attached to an isometric force transducer (Radnoti Inc., Monrovia, Calif.) and the data recorded with a Ponemah physiology platform (Gould Instrument systems, Inc., Valley View, Ohio) and placed in an oxygenated (95% $O_2$, 5% $CO_2$) tissue bath containing the buffer solution. The tissues are adjusted to 1 gram resting tension and allowed to stabilize for about one hour before testing. The integrity of the rings can be tested with norepinepherin (Sigma Co., St. Louis, Mo.) and Carbachol, a muscarinic acetylcholine agonist (Sigma Co.). After integrity is checked, the rings are washed three times with fresh buffer and allowed to rest for about one hour. To test a sample for vasodilatation, or relaxation of the aortic ring tissue, the rings are contracted to two grams tension and allowed to stabilize for fifteen minutes. A zsig33 polypeptide sample is then added to 1, 2 or 3 of the 4 baths, without flushing, and tension on the rings recorded and compared to the control rings containing buffer only. Enhancement or relaxation of contractility by zsig33 polypeptides, their agonists and antagonists is directly measured by this method, and it can be applied to other contractile tissues such as gastrointestinal tissues.

The activity of molecules of the present invention can be measured using a variety of assays that measure for example, stimulation of gastrointestinal contractility, modulation of nutrient uptake, modulation of growth hormones, modulation of the secretion of digestive enzymes and hormones, and/or modulation of secretion of enzymes and/or hormones in the pancreas. Of particular interest are changes in contractility of smooth muscle cells. For example, the contractile response of segments of mammalian duodenum or other gastrointestinal smooth muscles tissue (Depoortere et al., *J. Gastrointestinal Motility* 1:150-159, 1989). An exemplary in vivo assay uses an ultrasonic micrometer to measure the dimensional changes radially between commissures and longitudinally to the plane of the valve base (Hansen et al., *Society of Thoracic Surgeons* 60:S384-390, 1995).

Gastric motility is generally measured in the clinical setting as the time required for gastric emptying and subsequent transit time through the gastrointestinal tract. Gastric emptying scans are well known to those skilled in the art, and briefly, comprise use of an oral contrast agent, such as barium, or a radiolabeled meal. Solids and liquids can be measured independently. A test food or liquid is radiolabeled with an isotope (e.g. $^{99m}$Tc), and after ingestion or administration, transit time through the gastrointestinal tract and gastric emptying are measured by visualization using gamma cameras (Meyer et al., *Am. J. Dig. Dis.* 21:296, 1976; Collins et al., *Gut* 24:1117, 1983; Maughan et al., *Diabet. Med.* 13 9 *Supp.* 5:S6-10, 1996 and Horowitz et al., *Arch. Intern. Med.* 145: 1467-1472, 1985). These studies may be performed before and after the administration of a promotility agent to quantify the efficacy of the drug.

Proliferation can be measured using cultured cells or in vivo by administering molecules of the claimed invention to an appropriate animal model. Generally, proliferative effects are observed as an increase in cell number and therefore, may include inhibition of apoptosis, as well as mitogenesis. Cultured cells include cells derived from the pituitary, hypothalamus, hippocampus, as well as from the gastrointestinal tract, kidney, stomach, duodenum, and jejunum. One of skill in the art will be able to identify such cell lines from, for example, ATCC (Manasas, Va.) which are instrumental in studying the effects of binding GHS-R to zsig33. Assays measuring cell proliferation are well known in the art. For example, assays measuring proliferation include such assays as chemosensitivity to neutral red dye (Cavanaugh et al., *Investigational New Drugs* 8:347-354, 1990), incorporation of radiolabelled nucleotides (Cook et al., *Analytical Biochem.* 179:1-7, 1989), incorporation of 5-bromo-2'-deoxyuridine (BrdU) in the DNA of proliferating cells (Porstmann et al., *J. Immunol Methods* 82:169-179, 1985), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988).

To determine if zsig33 is a chemotractant in vivo, zsig33 can be given by intradermal or intraperitoneal injection. Characterization of the accumulated leukocytes at the site of injection can be determined using lineage specific cell surface markers and fluorescence immunocytometry or by immuno-histochemistry (Jose, *J. Exp. Med.* 179:881-87, 1994). Release of specific leukocyte cell populations from bone marrow into peripheral blood can also be measured after zsig33 injection.

There is evidence to suggest that factors that stimulate specific cell types down a pathway towards terminal differentiation or dedifferentiation affect the entire cell population originating from a common precursor or stem cell. Thus, zsig33 polypeptides may stimulate inhibition or proliferation of endocrine and exocrine cells of the stomach, lung, pituitary, hypothalamus, hippocampus, kidney, duodenum, jejunum, small intestine, skeletal muscle, and pancreas.

Molecules of the present invention may, while stimulating proliferation or differentiation of gastrointestinal/epithelial cells, inhibit proliferation or differentiation of neural cells, by virtue of their effect on common precursor/stem cells. The novel polypeptides of the present invention are useful to study neural and epithelial stem cells and stomach, lung, pituitary, hypothalamus, hippocampus, kidney, duodenum, jejunum, small intestine, skeletal muscle, and pancreas progenitor cells, both in vivo and ex vivo.

Assays measuring differentiation include, for example, measuring cell-surface markers associated with stage-specific expression of a tissue, enzymatic activity, functional activity or morphological changes (Watt, *FASEB,* 5:281-284, 1991; Francis, *Differentiation* 57:63-75, 1994; Raes, *Adv. Anim. Cell Biol. Technol. Bioprocesses,* 161-171, 1989).0

The zsig33 polypeptides of the present invention can be used to study proliferation or differentiation in stomach, lung, pituitary, hypothalamus, hippocampus, kidney, duodenum, jejunum, small intestine, skeletal muscle, and pancreas. Such methods of the present invention generally comprise incubating cells derived from these tissues in the presence and absence of zsig33 polypeptide, monoclonal antibody, agonist or antagonist thereof and observing changes in cell proliferation or differentiation. Cell lines from these tissues are commercially available from, for example, American Type Culture Collection (Manasas, Va.).

Proteins, including peptides resulting from alternative splicing, and fragments, of the present invention are useful for studying gastrointestinal contractility, modulation of nutrient uptake, modulation of growth hormones, modulation of the secretion of digestive enzymes and hormones, and/or modulation of secretion of enzymes and/or hormones in the pancreas. Zsig33 molecules, variants, and fragments can be applied in isolation, or in conjunction with other molecules (growth factors, cytokines, etc.) in stomach, lung, kidney, duodenum, jejunum, small intestine, skeletal muscle, and pancreas.

Potential uses of growth hormone are extensive and include treatment of diseases and conditions associated with bone formation (such as, for example, treatment of osteoporosis, acceleration of bone formation and repair, stimulating osteoblasts, bone remodeling and cartilage growth, and skeletal dysplasia); immunity (such as, for example, stimulating the immune system, treating immunosuppressed patients); obesity, and metabolic disorders (such as, for example, preventing catabolic side effects of glucocorticoids, treatment of obesity and growth retardation related to obesity, attenuation of protein catabolic responses after surgery, reducing cachexia and protein loss due to chronic illness such as cancer or AIDS); dwarfism (such as, for example, treating growth retardation and physiological short stature including growth hormone deficiency and chromic illness, and intrauterine growth retardation); wound healing (such as, for example, accelerating wound repair, accelerating recovery of burn patients and treating patients with delayed wound healing); reproduction (such as, for example, as an adjuvant treatment for ovulation induction); as well as conditions associated with stress; conditions associated with kidney and lung dysfunction; conditions associated with aging and the elderly, including, muscle strength, bone fragility and skin thickness; and neuroendocrine activities such as sleep. Thus, growth hormone secretagogues, including zsig33 polypeptides, would be useful to treat conditions associated with these disorders. Assays measuring the release of growth hormone are known in the art.

An association between gastrointestinal function and brain function has been observed for other hormones in this class. As an example, secretin infusion in autistic children resulted in amelioration of the gastrointestinal symptoms as well as a dramatic improvement in behavior (improved eye contact, alertness and expansion of expressive language). See Hovrath, K. et al., *J. Assoc. Acad. Minor Phys* 9(1):9-15, 1998. Similarly, a study of the upper gastrointestinal tract in autistic children with gastrointestinal symptoms showed that many had reflux esophagitis, chronic gastritis, and chronic duodenitis, as well as an elevated number of Paneth's cells in the duodenal crypts compared to non-autistic children. See Horvath, K. et al., *J. Pediatr.* 135(5):559-563, 1999. The administration of secretin to these autistic children resulted in increased pancreatico-biliary fluid output and higher fluid output. Gastrointestinal disorders, especially reflux esophagitis and disaccharide malabsoprtion may contribute to the behavioral problems of the non-verbal autistic patients. The observed increase in pancreatico-biliary secretion after secretin infusion suggests an upregulation of secretin receptors. As a member of the gut-hormone family of proteins, zsig33, by binding to its receptor, may have effects on neural development and/or utilization.

Proteins of the present invention are useful for delivery of therapeutic agents such as, but not limited to, proteases, radionuclides, chemotherapy agents, and small molecules. Effects of these therapeutic agents can be measured in vitro using cultured cells, ex vivo on tissue slices, or in vivo by administering molecules of the claimed invention to the appropriate animal model. An alternative in vivo approach for assaying proteins of the present invention involves viral delivery systems. Exemplary viruses for this purpose include adenovirus, retrovirus, herpesvirus, lentivirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161-89, 1994; and J. T. Douglas and D. T. Curiel, *Science & Medicine* 4:44-53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022-2032, 1998; Raper, S. E. et al., *Human Gene Therapy* 9:671-679, 1998). In addition, deletion of E2b is reported to reduce immune responses (Amalfitano, A. et al., *J. Virol.* 72:926-933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615-623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (see Gamier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

As soluble or cell-surface proteins, the activity of zsig33 and GHS-R polypeptides, respectively can be measured by a silicon-based biosensor microphysiometer which measures the extracellular acidification rate or proton excretion associated with cell-surface protein interactions and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol.* 228:84-108, 1997; Arimilli, S. et al., *J. Immunol. Meth.* 212:49-59, 1998; Van Liefde, I. et al., *Eur. J. Pharmacol.* 346:87-95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zsig33 proteins, their, agonists, and antagonists. Preferably, the microphysiometer is used to measure responses of a eukaryotic cell expressing GHS-R on its cell surface, compared to a control eukaryotic cell that does not express GHS-R. Such GHS-R expressing cells include cells which express an endogenous GHS-R polynucleotide sequence and cells into which the polynucleotide sequence, or a fragment or chimera containing a portion of the GHS-R polynucleotide sequence, i.e., SEQ ID NOs:4 or 6, has been transfected. Differences, measured by a change in the response of cells exposed to zsig33 polypeptide, relative to a control not exposed to zsig33, are a direct measurement of zsig33-modulated cellular responses. Moreover, such zsig33-modulated responses can be assayed under a variety of stimuli. The present invention provides a method of identifying agonists and antagonists of zsig33 protein, comprising providing cells responsive to a zsig33 polypeptide, culturing a first portion of the cells in the absence of a test compound, culturing a second portion of the cells in the presence of a test compound, and detecting a change in a cellular response of the second portion of the cells as compared to the first portion of the cells. The change in cellular response is shown as a measurable change in extracellular acidification rate. Moreover, culturing a third portion of the cells in the presence of zsig33 polypeptide and the absence of a test compound provides a positive control for the zsig33-stimulated cells, and a control to compare the agonist activity of a test compound with that of the zsig33 polypeptide. Antagonists of zsig33 can be identified by exposing the cells to zsig33 protein in the presence and absence of the test compound, whereby a reduction in zsig33-stimulated activity is indicative of agonist activity in the test compound.

Moreover, zsig33 can be used to identify additional cells, tissues, or cell lines which express GHS-R, or other cells which respond to a zsig33-stimulated pathway. The microphysiometer, described above, can be used to rapidly identify cells that are responsive to zsig33 of the present invention. Cells can be cultured in the presence or absence of zsig33 polypeptide. Those cells which elicit a measurable change in extracellular acidification in the presence of zsig33 are responsive to zsig33. Such cell lines, can be used to identify additional isoforms of zsig33, antagonists and agonists of zsig33 polypeptide as described above. Similarly, the microphysiometer can be used in this method to identify variants of GHS-R which maintain activation by zsig33.

Additional assays provided by the present invention include the use of hybrid receptor polypeptides. These hybrid polypeptides fall into two general classes. Within the first class, the intracellular domain of GHS-R, comprising approximately residues 327 to 366 of SEQ ID NO:5, is joined to the ligand-binding domain of a second receptor. It is preferred that the second receptor be a G protein-coupled receptor, such as the motilin receptor, GPR38. The hybrid receptor will further comprise transmembrane domains, which may be derived from either receptor. A DNA construct encoding the hybrid receptor is then inserted into a host cell. Cells expressing the hybrid receptor are cultured in the presence of motilin and assayed for a response. This system provides a means for analyzing signal transduction mediated by GHS-R while using readily available ligands. This system can also be used to determine if particular cell lines are capable of responding to signals transduced by GHS-R. A second class of hybrid receptor polypeptides comprise the extracellular (ligand-binding) domain of GHS-R (approximately residues 1 to 326 of SEQ ID NO:5) with a cytoplasmic domain of a second receptor, preferably a G protein-coupled receptor, and transmembrane domains. The transmembrane domains may be derived from either receptor. Hybrid receptors of this second class are expressed in cells known to be capable of responding to signals transduced by the second receptor. Together, these two classes of hybrid receptors enable the use of a broad spectrum of cell types within receptor-based assay systems.

Assays can be used to measure other cellular responses, that include, chemotaxis, adhesion, changes in ion channel influx, regulation of second messenger levels and neurotransmitter release. Such assays are well known in the art. See, for example, in "Basic & Clinical Endocrinology Ser., Vol. Vol. 3," *Cytochemical Bioassays: Techniques & Applications*, Chayen; Chayen, Bitensky, eds., Dekker, New York, 1983.

In view of the tissue distribution (i.e., stomach, lung, pituitary, hypothalamus, hippocampus, kidney, duodenum, jejunum, small intestine, skeletal muscle, and pancreas) observed for zsig33 and GHS-R expression, agonists (including native or synthetic peptides) and antagonists of zsig33 have enormous potential in both in vitro and in vivo applications. Compounds identified as zsig33 agonists and antagonists are useful for studying gastrointestinal contractility, modulation of nutrient uptake, modulation of growth hormones, modulation of the secretion of digestive enzymes and hormones, and/or modulation of secretion of enzymes and/or hormones in the pancreas in vitro and in vivo. For example, zsig33 and agonist compounds are useful as components of defined cell culture media, and may be used alone or in combination with other cytokines and hormones to replace serum that is commonly used in cell culture. Agonists are thus useful in specifically promoting the growth and/or development of cells of gastrointestinal cells such as G cells, enterochromaffin cells and the epithelial mucosa of the stomach, duodenum, jejunum, as well as kidney, lung, and pancreas cells in culture. Additionally, zsig33 polypeptides and zsig33 agonists, including small molecules are useful as a research reagent, such as for the expansion, differentiation, and/or cell-cell interactions of stomach, lung, kidney, duodenum, jejunum, small intestine, skeletal muscle, and pancreas. Zsig33 polypeptides are added to tissue culture media for these cell types.

The family of gut-brain peptides has been associated with neurological and CNS functions. For example, NPY, a peptide with receptors in both the brain and the gut has been shown to stimulate appetite when administered to the central nervous system (Gehlert, *Life Sciences* 55(6):551-562, 1994). Motilin immunoreactivity has been identified in different regions of the brain, particularly the cerebellum, and in the pituitary (Gasparini et al., *Hum. Genetics* 94(6):671-674, 1994). Motilin has been found to coexist with neurotransmitter γ-aminobutyric acid in cerebellum (Chan-Patay, *Proc. Sym. 50th Anniv Meet. Br. Pharmalog. Soc.:* 1-24, 1982). Physiological studies have provided some evidence that motilin has an affect on feeding behavior (Rosenfield et al., *Phys. Behav.* 39(6):735-736, 1987), bladder control, pituitary growth hormone release. Other gut-brain peptides, such as CCK, enkephalin, VIP and secretin have been shown to be involved in control of blood pressure, heart rate, behavior, and pain modulation, in addition to be active in the digestive system. Therefore, the binding of zsig33 to GHS-R, or some portion thereof, could be expected to have some neurological association.

Additionally, other members of the gut-brain peptides, such as CCK, gastrin, and the like, have been shown to modulate secretion of pancreatic enzymes and hormones. The location for GSH-R in the pancreas (See Guan, X. M. et al., *Mol. Brain Res.* 48: 23-29, 1997) suggests that the binding of zsig33 peptides to GHS-R can be used to modulate secretion of pancreatic enzymes and hormones.

Similarly, other members of the gut-brain peptides are known to modulate the secretion of endogenous proteins, such as the manner in which glucagon modulates the secretion of insulin. One advantage of growth hormone secretagogues, in general, is their ability to amplify endogenous pulsatile growth hormone secretion while maintaining normal feedback mechanisms. Another important effect is the ability to restore serum insulin-like growth factor-I (IGF-I) levels in elderly adults to concentrations similar to those of young adults. See Hansen, *ibid*. Thus, as a ligand for GHS-R, zsig33 can be useful for modulating secretion of growth hormone and insulin-like growth factor I. Additionally, zsig33 peptides can be used to modulate the secretion of non-zsig33 proteins such as, for example, GLP-1, somatostatin, and the like.

Using site-specific changes in the amino acid and DNA sequences of the present invention analogs can be made that are either antagonists, agonists or partial agonists (Macielay et al., *Peptides: Chem. Struct. Biol*. pp. 659, 1996). Antagonists are useful for clinical conditions associated with gastrointestinal hypermotility such as diarrhea and Crohn's disease. Antagonists are also useful as research reagents for characterizing sites of ligand-receptor interaction.

Antagonists are also useful as research reagents for characterizing sites of interactions between members of complement/anti-complement pairs as well as sites of cell-cell interactions. Inhibitors of zsig33 activity (zsig33 antagonists) include anti-zsig33 antibodies, and soluble zsig33 polypeptides (such as in SEQ ID NO:2) as well as other peptidic and non-peptidic agents (including ribozymes).

Zsig33 can also be used to identify inhibitors (antagonists) of its activity. Test compounds are added to the assays disclosed herein to identify compounds that inhibit the activity of zsig33. In addition to those assays disclosed herein, samples can be tested for inhibition of zsig33 activity within a variety of assays designed to measure ligand/receptor binding or the stimulation/inhibition of zsig33-dependent cellular responses. For example, zsig33-responsive cell lines can be transfected with a reporter gene construct that is responsive to a zsig33-stimulated cellular pathway. Reporter gene constructs of this type are known in the art, and will generally comprise a DNA response element operably linked to a gene encoding an assayable protein, such as luciferase, or a metabolite, such as cyclic AMP. DNA response elements can include, but are not limited to, cyclic AMP response elements (CRE), hormone response elements (HRE), insulin response element (IRE) (Nasrin et al., *Proc. Natl. Acad. Sci. USA* 87:5273-7, 1990) and serum response elements (SRE) (Shaw et al. *Cell* 56: 563-72, 1989). Cyclic AMP response elements are reviewed in Roestler et al., *J. Biol. Chem.* 263 (19):9063-6; 1988 and Habener, *Molec. Endocrinol.* 4 (8):1087-94; 1990. Hormone response elements are reviewed in Beato, *Cell* 56:335-44; 1989. One likely reporter gene construct would contain a G protein-linked receptor that, upon binding a ligand, would signal intracellularly through, for example, a cyclic AMP response element. One likely reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:19094-29101, 1994; Schenborn and Goiffin, *Promega Notes* 41:11, 1993). Luciferase assay kits are commercially available from, for example, Promega Corp., Madison, Wis. Target cell lines of this type can be used to screen libraries of chemicals, cell-conditioned culture media, fungal broths, soil samples, water samples, and the like. Candidate compounds, solutions, mixtures or extracts are tested for the ability to inhibit the activity of zsig33 on the target cells, as evidenced by a decrease in zsig33 stimulation of reporter gene expression. Assays of this type will detect compounds that directly block the binding of zsig33 to GHS-R, as well as compounds that block processes in the cellular pathway subsequent to binding In the alternative, compounds or other samples can be tested for direct blocking of the binding of zsig33 to GHS-R using zsig33 tagged with a detectable label (e.g., $^{125}$I, biotin, horseradish peroxidase, FITC, and the like). Within assays of this type, the ability of a test sample to inhibit the binding of labeled zsig33 to the GHS-R is indicative of inhibitory activity, which can be confirmed through secondary assays. Receptors used within binding assays may be cellular receptors, such as GHS-R, soluble receptors, or isolated, immobilized receptors. Additionally, assays of this sort can be used to identify functional variants of zsig33 peptides, as well as, GHS-R variants.

Another assay uses cell lines expressing $G_{\alpha16}$ and the calcium sensitive photoprotein, aequorin, in a screening system for agonist activity. This system (described by Stables, J. et al., *Anal. Biochem.* 252:115-126, 1997) uses the $G_{\alpha16}$ protein to couple with any G protein-linked receptor. Binding the receptor results in an increase in intracellular calcium concentrations. The cells are pre-incubated in coelenterazine and the intracellular calcium reacts with aequorin (which has also been transfected into the cells) and coelenterazine resulting in a luminescent response. Cell lines from pituitary, hypothalamus, and pancreas would be useful for GHS-R in this assay.

Also, zsig33 polypeptides, agonists or antagonists thereof may be therapeutically useful for promoting wound healing, for example, in stomach, lung, pituitary, hypothalamus, hippocampus, kidney, duodenum, jejunum, small intestine, skeletal muscle, and pancreas tissues. To verify the presence of this capability in zsig33 polypeptides, agonists or antagonists of the present invention, such zsig33 polypeptides, agonists or antagonists are evaluated with respect to their ability to facilitate wound healing according to procedures known in the art. If desired, zsig33 polypeptide performance in this regard can be compared to growth factors, such as EGF, NGF, TGF-α, TGF-β, insulin, IGF-I, IGF-II, fibroblast growth factor (FGF) and the like. In addition, zsig33 polypeptides or agonists or antagonists thereof may be evaluated in combination with one or more growth factors to identify synergistic effects.

GHS-R can also be used for purification of zsig33. The polypeptide (i.e., SEQ ID NO:5) is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing zsig33 polypeptides are passed through the column one or more times to allow zsig33 polypeptides to bind to GHS-R polypeptides. The zsig33 polypeptide is then eluted using changes in salt concentration, chaotropic agents (guanidine HCl), or pH to disrupt receptor binding.

An assay system that uses a ligand-binding receptor (or an antibody, one member of a complementary/anti-complementary pair or other cell-surface binding protein) or a binding fragment thereof, and a commercially available biosensor instrument (BIAcore, Pharmacia Biosensor, Piscataway, N.J.) may be advantageously employed. Such receptor (i.e., GHS-R), antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member, ligand or fragment is covalently attached, using amine or sulfhydryl chemistry, to dextran fibers that are attached to gold film within the flow cell. A test sample is passed through the cell. If a ligand, epitope, or opposite member of the complementary/anti-complementary pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

GHS-R polypeptides and other receptor polypeptides which bind ligand polypeptides can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253:545-48, 1991; Cunningham et al., *Science* 245:821-25, 1991).

A "soluble protein" is a protein that is not bound to a cell membrane. Soluble proteins are most commonly ligand-binding receptor polypeptides that lack transmembrane and cytoplasmic domains. Soluble proteins can comprise additional amino acid residues, such as affinity tags that provide for purification of the polypeptide or provide sites for attachment of the polypeptide to a substrate, or immunoglobulin constant region sequences. Many cell-surface proteins have naturally occurring, soluble counterparts that are produced by proteolysis or translated from alternatively spliced mRNAs. Proteins are said to be substantially free of transmembrane and intracellular polypeptide segments when they lack sufficient portions of these segments to provide membrane anchoring or signal transduction, respectively.

Molecules of the present invention can be used to identify and isolate other isoforms of GHS-R, or other G protein-coupled receptors, cell-surface binding proteins, or members of complement/anti-complement pairs involved in gut-hormone interactions. For example, proteins and peptides of zsig33 can be immobilized on a column and membrane preparations run over the column (*Immobilized Affinity Ligand Techniques*, Hermanson et al., eds., Academic Press, San Diego, Calif., 1992, pp. 195-202). Proteins and peptides can also be radiolabeled (*Methods in Enzymol.*, vol. 182, "Guide to Protein Purification", M. Deutscher, ed., Acad. Press, San Diego, 1990, 721-37) or photoaffinity labeled (Brunner et al., *Ann. Rev. Biochem.* 62:483-514, 1993 and Fedan et al., *Biochem. Pharmacol.* 33:1167-80, 1984) and specific cell-surface proteins can be identified.

The molecules of the present invention will be useful in gastrointestinal contractility, modulation of nutrient uptake, modulation of growth hormones, modulation of the secretion of digestive enzymes and hormones, and/or modulation of secretion of enzymes and/or hormones in the pancreas. The molecules of the present invention can be used to modulate ligand-receptor binding or to treat or prevent development of pathological conditions in such diverse tissue as stomach, pituitary, hypothalamus, hippocampus, lung, kidney, duodenum, jejunum, small intestine, skeletal muscle, and pancreas. In particular, certain diseases may be amenable to such diagnosis, treatment or prevention. The molecules of the present invention can be used to modulate inhibition and proliferation of neurons and myocytes in stomach, pituitary, hypothalamus, hippocampus, lung, kidney, duodenum, jejunum, small intestine, skeletal muscle, and pancreas. The polypeptides, nucleic acid and/or antibodies of the present invention can be used in diagnosis, treatment or prevention of disorders associated with, for example, gastric reflux, gastroparesis, modulation of secretion of pituitary hormones, including growth hormone, and or growth hormone stimulating hormone, Crohn's Disease, metabolic wasting, gastric ulcers, weight management, fertility, diseases of the developing reproductive system, and degenerative diseases.

Polynucleotides encoding zsig33 and/or GHS-R polypeptides are useful within gene therapy applications where it is desired to increase or inhibit zsig33/GHS-R binding activity. If a mammal has a mutated or absent zsig33 or GHS-R gene, that gene can be introduced into the cells of the mammal In one embodiment, a gene encoding the zsig33 or GHS-R polypeptide is introduced in vivo in a viral vector. Such vectors include an attenuated or defective DNA virus, such as, but not limited to, herpes simplex virus (HSV), papillomavirus, Epstein Barr virus (EBV), retrovirus, adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-30, 1991); an attenuated adenovirus vector, such as the vector described by Stratford-Perricaudet et al., *J. Clin. Invest.* 90:626-30, 1992; and a defective adeno-associated virus vector (Samulski et al., *J. Virol.* 61:3096-101, 1987; Samulski et al., *J. Virol.* 63:3822-8, 1989).

In addition, as a cell surface molecule, GHS-R polypeptide can be used as a target to introduce gene therapy into a cell. This application would be particularly appropriate for introducing therapeutic genes into cells in which GHS-R is normally expressed, such as pituitary, hypothalamus, and hippocampus cells. For example, viral gene therapy, such as described above, can be targeted to specific cell types in which express a cellular receptor, such as GHS-R polypeptide, rather than the viral receptor. Antibodies, or other molecules such as zsig33 peptides that recognize GHS-R molecules on the target cell's surface can be used to direct the virus to infect and administer gene therapeutic material to that target cell. See, Woo, S. L. C, *Nature Biotech.* 14:1538, 1996; Wickham, T. J. et al, *Nature Biotech.* 14:1570-1573, 1996; Douglas, J. T et al., *Nature Biotech.* 14:1574-1578, 1996; Rihova, B., *Crit. Rev. Biotechnol.* 17:149-169, 1997; and Vile, R. G. et al., *Mol. Med. Today* 4:84-92, 1998. For example, a bispecific antibody containing a virus-neutralizing Fab fragment coupled to a GHS-R-specific antibody can be used to direct the virus to cells expressing the GHS-R and allow efficient entry of the virus containing a genetic element into the cells. See, for example, Wickham, T. J., et al., *J. Virol.* 71:7663-7669, 1997; and Wickham, T. J., et al., *J. Virol.* 70:6831-6838, 1996.

In another embodiment, a zsig33 or GHS-R gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413-7, 1987; Mackey et al., *Proc. Natl. Acad. Sci. USA* 85:8027-31, 1988). The use of lipofection to introduce exogenous genes into specific organs in vivo has certain practical advantages. Molecular targeting of liposomes to specific cells represents an area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Similarly, the zsig33 polynucleotides (SEQ ID NO:1 or SEQ ID NO:3) can be used to target specific tissues such as stomach, pituitary, hypothalamus, hippocampus, lung, kidney, duodenum, jejunum, small intestine, skeletal muscle, and pancreas. It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7, 1992; Wu et al., *J. Biol. Chem.* 263:14621-4, 1988.

Various techniques, including antisense and ribozyme methodologies, can be used to inhibit zsig33 gene transcription and translation, such as to inhibit cell proliferation in vivo. Polynucleotides that are complementary to a segment of a zsig33-encoding polynucleotide (e.g., a polynucleotide as set forth in SEQ ID NOs:1 or 3) are designed to bind to zsig33-encoding mRNA and to inhibit translation of such mRNA. Such antisense polynucleotides are used to inhibit expression of zsig33 polypeptide-encoding genes in cell culture or in a subject.

Mice engineered to express the zsig33 or GHS-R gene, referred to as "transgenic mice," and mice that exhibit a complete absence of zsig33 or GHS-R gene function, referred to as "knockout mice," may also be generated (Snouwaert et al., Science 257:1083, 1992; Lowell et al., Nature 366:740-42, 1993; Capecchi, M. R., Science 244: 1288-1292, 1989; Palmiter, R. D. et al. Annu Rev Genet. 20: 465-499, 1986). For example, transgenic mice that over-express zsig33 or GHS-R, either ubiquitously or under a tissue-specific or tissue-restricted promoter can be used to ask whether over-expression causes a phenotype. For example, over-expression of a wild-type zsig33 or GHS-R polypeptide, polypeptide fragment or a mutant thereof may alter normal cellular processes, resulting in a phenotype that identifies a tissue in which zsig33 or GHS-R expression is functionally relevant and may indicate a therapeutic target for the zsig33, its agonists or antagonists. For example, a preferred transgenic mouse to engineer is one that over-expresses the GHS-R polypeptide (approximately amino acids 1 to 366 of SEQ ID NO:5), or the zsig33 polypeptide (amino acids 1 to 117 of SEQ ID NO:2). Moreover, such over-expression may result in a phenotype that shows similarity with human diseases. Similarly, knockout zsig33 and GHS-R mice can be used to determine where zsig33 is absolutely required in vivo. The phenotype of knockout mice is predictive of the in vivo effects of that a zsig33 antagonist, such as those described herein, may have. The human zsig33 cDNA can be used to isolate murine zsig33 mRNA, cDNA and genomic DNA, which are subsequently used to generate knockout mice. These mice may be employed to study the zsig33 and GHS-R genes and the proteins encoded thereby in an in vivo system, and can be used as in vivo models for corresponding human diseases. Moreover, transgenic mice expression of zsig33 or GHS-R antisense polynucleotides or ribozymes directed against zsig33, described herein, can be used analogously to transgenic mice described above.

Zsig33 polypeptides, variants, and fragments thereof, may be useful as replacement therapy for disorders associated with cell-cell interactions, including disorders related to, for example, stimulation of gastrointestinal contractility, modulation of nutrient uptake, modulation of growth hormones, modulation of the secretion of digestive enzymes and hormones, and modulation of secretion of enzymes and/or hormones in the pancreas.

A less widely appreciated determinant of tissue morphogenesis is the process of cell rearrangement: Both cell motility and cell-cell adhesion are likely to play central roles in morphogenetic cell rearrangements. Cells need to be able to rapidly break and probably simultaneously remake contacts with neighboring cells. See Gumbiner, B. M., Cell 69:385-387, 1992. As a secreted protein in stomach, pituitary, hypothalamus, hippocampus, lung, kidney, duodenum, jejunum, small intestine, skeletal muscle, and pancreas, zsig33 and GHS-R can play a role in intercellular rearrangement in these and other tissues.

Zsig33 gene may be useful as a probe to identify humans who have a defective zsig33 gene. The strong expression of zsig33 in stomach, kidney, small intestine, and pancreas, suggests that zsig33 polynucleotides or polypeptides can be used as an indication of aberrant growth in these tissues. Thus, polynucleotides and polypeptides of zsig33, and mutations to them, can be used a diagnostic indicators of cancer in these tissues.

Zsig33 binding proteins, such as an anti-zsig33 antibody, or GHS-R, may also be used within diagnostic systems for the detection of circulating levels of zsig33. Within a related embodiment, antibodies or other agents that specifically bind to GHS-R can be used to detect circulating receptor polypeptides. Elevated or depressed levels of ligand or receptor polypeptides may be indicative of pathological conditions, including cancer.

The polypeptides of the present invention are useful in studying cell adhesion and the role thereof in metastasis and may be useful in preventing metastasis, in particular metastasis in tumors of the stomach, pituitary, hypothalamus, hippocampus, lung, kidney, duodenum, jejunum, small intestine, small intestine, skeletal muscle, and pancreas. Similarly, polynucleotides and polypeptides of zsig33 may be used to replace their defective counterparts in tumor or malignant tissues.

The zsig33 and GHS-R polypeptides are expressed in the stomach, pituitary, hypothalamus, hippocampus, lung, kidney, duodenum, jejunum, skeletal muscle, and pancreas. Thus, zsig33 polypeptide pharmaceutical compositions of the present invention may be useful in prevention or treatment of disorders associated with pathological regulation or the expansion of stomach, pituitary, hypothalamus, hippocampus, lung, kidney, duodenum, jejunum, skeletal muscle, and pancreas.

The polynucleotides of the present invention may also be used in conjunction with a regulatable promoter, thus allowing the dosage of delivered protein to be regulated.

The zsig33 polynucleotides of SEQ ID NO:2 have been mapped to chromosome 3p26.1. Thus, the present invention also provides reagents which will find use in diagnostic applications. For example, the zsig33 gene, a probe comprising zsig33 DNA or RNA or a subsequence thereof can be used to determine if the zsig33 gene is present on chromosome 3p26.1 or if a mutation has occurred. Detectable chromosomal aberrations at the zsig33 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, Chest 108:255-65, 1995).

The peptides, variants, nucleic acid and/or antibodies of the present invention may be used in treatment of disorders associated with gastrointestinal contractility, modulation of growth hormone secretion, secretion of digestive enzymes, hormones and acids, gastrointestinal motility, recruitment of digestive enzymes; inflammation, particularly as it affects the gastrointestinal system; reflux disease and regulation of nutrient absorption. Specific conditions that will benefit from treatment with molecules of the present invention include, but are not limited to, diabetic gastroparesis, post-surgical gastroparesis, vagotomy, chronic idiopathic intestinal pseudo-obstruction and gastroesophageal reflux disease. Additional uses include, gastric emptying for radiological studies, stimulating gallbladder contraction and antrectomy.

The motor and neurological affects of molecules of the present invention make it useful for treatment of obesity and other metabolic disorders where neurological feedback modulates nutritional absorption. The molecules of the present invention are useful for regulating satiety, glucose absorption and metabolism, and neuropathy-associated gastrointestinal disorders.

Peptides of the present invention may be useful for evaluating functions of the hypothalamus-pituitary-adrenal axis by challenging the gastrointestinal system with zsig33 peptides, including variants, and measuring gastric motility and contractility, modulation of nutrient uptake, modulation of growth hormones, modulation of the secretion of digestive enzymes and hormones, or modulation of secretion of enzymes and/or hormones in the pancreas.

Additionally, molecules of zsig33 peptides may be used to detect or modulate the growth and/or differentiation of tumor cells which are expressing GHS-R peptides. Zsig33 peptides can be labeled with radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. These labeled polypeptides can be applied in vitro or in vivo and are especially useful to identify GHS-R receptors located on tumors in such tissues as, for example, brain, pancreas, kidney, duodenum, jejunum, and lung.

Molecules of the present invention are also useful as additives to anti-hypoglycemic preparations containing glucose and as adsorption enhancers for oral drugs which require fast nutrient action. Additionally, molecules of the present invention can be used to stimulate glucose-induced insulin release.

For pharmaceutical use, the proteins of the present invention can be administered orally, rectally, parenterally (particularly intravenous or subcutaneous), intracisternally, intravaginally, intraperitoneally, topically (as powders, ointments, drops or transdermal patch) bucally, or as a pulmonary or nasal inhalant. Intravenous administration will be by bolus injection or infusion over a typical period of one to several hours. In general, pharmaceutical formulations will include a zsig33 protein, alone, or in conjunction with a dimeric partner, in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of zsig33 is an amount sufficient to produce a clinically significant change in gastrointestinal contractility, modulation of nutrient uptake, modulation of growth hormones, modulation of the secretion of digestive enzymes and hormones, and modulation of secretion of enzymes and/or hormones in the pancreas, in stomach, lung, kidney, duodenum, jejunum, skeletal muscle, and pancreas tissues.

The invention is further illustrated by the following non-limiting examples.

EXAMPLES

Example 1

Tissue Distribution of zsig33

Analysis of tissue distribution of zsig33 was performed using Human Multiple Tissue Blots and Human RNA Master dot blots from Clontech (Palo Alto, Calif.). The probe was approximately 40 bp oligonucleotide ZC12,494 (SEQ ID NO:13). The probe was end labeled using T4 Polynucleotide Kinase (Life Technologies, Inc., Gaithersburg, Md.) and T4 Polynucleotide Kinase Forward Buffer (Life Technologies, Inc.). The probe was purified using a NUCTRAP push columns (Stratagene, La Jolla, Calif.). EXPRESSHYB (Clontech) solution was used for prehybridization and as a hybridizing solution for the Northern blots. Hybridization took place at 42° C., and the blots were washed in 2×SSC and 0.05% SDS at RT, followed by a wash in 1×SSC and 0.1% SDS at 71° C. An approximately 600 bp transcript was observed as a strong signal in stomach, with weaker signals seen in pancreas and small intestine.

Example 2

A. Gut Northern Tissue Blot

A Northern blot was prepared using mRNA from the following sources:
1. RNA from Human Colorectal Andenocarcinoma cell line SW480 (Clontech, Palo Alto, Calif.)
2. RNA from human small intestine tissue (Clontech)
3. RNA from human stomach tissue (Clontech)
4. Human Intestinal Smooth Muscle cell line (Hism; ATCC No. CRL-1692; American Type Culture Collection, 12301 Parklawn Drive, Rockville, Md.)
5. Normal Human Colon cell line (FHC; ATCC No. CRL-1831; American Type Culture Collection)
6. Human Normal Fetal Small Intestine cell line (FHs74 Int.; ATCC No. CCL241; American Type Culture Collection).

Total RNAs were isolated from Hism, FHC and FHs74 Int. by acid guanidium method (Chomczynski et al., *Anal. Biochem.* 162:156-159, 1987). The polyA$^+$ RNAs were selected by eluting total RNA through a column that retains polyA$^+$ RNAs (Aviv et al., *Proc. Nat. Acad. Sci.* 69:1408-1412, 1972). 2 mg polyA$^+$ RNA from each sample was separated out in a 1.5% agarose gel in 2.2 M formaldehyde and phosphate buffer. The RNAs were transferred onto Nytran membrane (Schleicher and Schuell, Keene, N.H.) in 20×SSC overnight. The blot was treated in the UV Stratalinker 2400 (Stratagene, La Jolla, Calif.) at 0.12 Joules. The bolt was then baked at 80° C. for one hour.

Using the full length cDNA (shown in SEQ ID NO: 1) amplified by PCR approximately 50 ng of zsig33 DNA and 42.5 ml water was radiolabeled with $^{32}$P dCTP using a Rediprime pellet kit (Amersham, Arlington Heights, Ill.) according to the manufacturer's specifications. The blot was hybridized in EXPRESSHYB (Clontech) at 55° C. overnight. The blot was washed at room temp. in 2×SSC and 0.1% SDS, then in 2×SSC and 0.1% SDS at 65° C., and finally at 65° C. in 0.1×SSC and 0.1% SDS. Results showed that zsig33 hybridized to stomach RNA and not to other RNAs from other tissue origins.

B. Tumor Northern Blot

A Northern Territory™-Human Tumor Panel Blot II (Invitrogen, San Diego, Calif.) and a Northern Territory™-Human Stomach Tumor Panel Blot (Invitrogen) were analyzed for expression patterns of zsig33 RNA.

The Human Tumor Panel Blot contained 20 mg of total RNA per lane and was run on a 1% denaturing formaldehyde gel. The blot contained RNA from: esophageal tumor, normal esophagus, stomach tumor, normal stomach, colon tumor, normal colon, rectal tumor and normal rectum. The Stomach Tumor Panel Blot contained total RNA isolated human and normal tissues of four separate donors. 20 mg RNA was used for each sample lane and the lanes alternated a normal and tumor set from each donor.

Probes that were approximately 40 bp oligonucleotide ZC12,494 (SEQ ID NO: 11) were prepared. The probes were end labeled using T4 Polynucleotide Kinase (Life Technologies, Inc., Gaithersburg, Md.) and T4 Polynucleotide Kinase Forward Buffer (Life Technologies, Inc.). The probes were purified using a NUCTRAP push columns (Stratagene, La Jolla, Calif.). The tumor blot and the stomach blot were both treated in the same way. EXPRESSHYB (Clontech) solution was used for prehybridization and as a hybridizing solution for the Northern blots. Hybridization took place at 42° C., and the blots were washed in 0.1×SSC and 0.01% SDS at 60° C., followed by a wash in 0.1×SSC and 0.1% SDS at 70° C. The results clearly indicate that zsig33 is exclusively expressed in normal stomach tissue in both the Human Tumor Panel and the Human Stomach Tumor Panel.

Example 3

Protein Purification

Purification Conditions for zsig33 with N- and C-terminal EE Tags:

*E. coli, Pichia*, CHO and BHK cells are transfected with expression vectors containing the DNA sequence of SEQ ID NO:1, or a portion thereof, operably linked to a polynucleotide encoding a Glu-Glu tag (SEQ ID NO:12). Zsig33 protein is expressed in the conditioned media of the *E. coli, Pichia methanolica*, and or chinese hamster ovary (CHO) cells. For zsig33 expressed in *E. coli* and *Pichia*, the media is not concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then concentrated to about 1.3 liters using a Millipore ProFlux A30 tangential flow concentrator fitted with a 3000 kDa cutoff Amicon (Bedford, Mass.) S10Y3 membrane. The concentrated material is again sterile-filtered with the Gelman filter, as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). A 50.0 ml sample of anti-EE Sepharose, prepared as described below, is added and the mixture gently agitated on a Wheaton (Millville, N.J.) roller culture apparatus for 18.0 h at 4° C.

The mixture is then poured into a 5.0×20.0 cm Econo-Column (Bio-Rad, Laboratories, Hercules, Calif.), and the gel is washed with 30 column volumes of phosphate buffered saline (PBS). The unretained flow-through fraction is discarded. Once the absorbance of the effluent at 280 nM is less than 0.05, flow through the column is reduced to zero, and the anti-EE Sepharose gel is washed with 2.0 column volumes of PBS containing 0.2 mg/ml of EE peptide (AnaSpec, San Jose, Calif.). The peptide that is used has the sequence GluTyrMetProValAsp. After 1.0 h at 4° C., flow is resumed and the eluted protein collected. This fraction is referred to as the peptide elution. The anti-EE Sepharose gel is then washed with 2.0 column volumes of 0.1 M glycine, pH 2.5, and the glycine wash is collected separately. The pH of the glycine-eluted fraction is adjusted to 7.0 by the addition of a small volume of 10×PBS and stored at 4° C. for future analysis, if needed.

The peptide elution is concentrated to 5.0 ml using a 15,000 molecular weight cutoff membrane concentrator (Millipore, Bedford, Mass.), according to the manufacturer's instructions. The concentrated peptide elution is then separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC (PerSeptive BioSystems, Framingham, Mass.). Two-ml fractions are collected and the absorbance at 280 nM monitored. The first peak of material absorbing at 280 nM and eluting near the void volume of the column is collected. This fraction is pure zsig33 NEE or zsig33 CEE. The pure material is concentrated as described above, analyzed by SDS-PAGE and Western blotting with anti-EE antibodies, aliquoted, and stored at −80° C. according to standard procedures.

Preparation of Anti-EE Sepharose:

A 100 ml bed volume of protein G-Sepharose (Pharmacia, Piscataway, N.J.) is washed 3 times with 100 ml of PBS containing 0.02% sodium azide using a 500 ml Nalgene 0.45 micron filter unit. The gel is washed with 6.0 volumes of 200 mM triethanolamine, pH 8.2 (TEA, Sigma, St. Louis, Mo.). and an equal volume of EE antibody solution containing 900 mg of antibody is added. After an overnight incubation at 4° C., unbound antibody is removed by washing the resin with 5 volumes of 200 mM TEA as described above. The resin is resuspended in 2 volumes of TEA, transferred to a suitable container, and dimethylpimilimidate-2HCl (Pierce, Rockford, Ill.), dissolved in TEA, is added to a final concentration of 36 mg/ml of gel. The gel is rocked at room temperature for 45 min and the liquid is removed using the filter unit as described above. Nonspecific sites on the gel are then blocked by incubating for 10 min at room temperature with 5 volumes of 20 mM ethanolamine in 200 mM TEA. The gel is then washed with 5 volumes of PBS containing 0.02% sodium azide and stored in this solution at 4° C.

Purification of Untagged zsig33:

*E. coli, Pichia*, CHO and BHK cells are transfected with expression vectors containing the DNA sequence of SEQ ID NO:1, or a portion thereof. The procedure described below is used for protein expressed in conditioned medium of *E. coli, Pichia methanolica*, and Chinese hamster ovary (CHO) and baby hamster kidney (BHK) cells. For zsig33 expressed in *E. coli* and *Pichia*, however, the medium is not be concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then be concentrated to about 1.3 liters using a Millipore ProFlux A30 tangential flow concentrator fitted with a 3000 kDa cutoff Amicon (Bedford, Mass.) S10Y3 membrane. The concentrated material is again sterile-filtered with the Gelman filter as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim).

Example 4

Synthesis of Peptides

Zsig33-1, a peptide corresponding to amino acid residue 24 (Gly) to amino acid residue 37 (Gln) of SEQ ID NO: 2, was synthesized by solid phase peptide synthesis using a model 431A Peptide Synthesizer (Applied Biosystems/Perkin Elmer, Foster City, Calif.). Fmoc-Glutamine resin (0.63 mmol/g; Advanced Chemtech, Louisville, Ky.) was used as the initial support resin. 1 mmol amino acid cartridges (Anaspec, Inc. San Jose, Calif.) were used for synthesis. A mixture of 2 (1-Hbenzotriazol-y-yl 1,1,3,3-tetrahmethylhyluronium hexafluorophosphate (HBTU), 1-hydroxybenzotriazol (HOBt), 2 m N,N-Diisolpropylethylamine, N-Methylpyrrolidone, Dichloromethane (all from Applied Biosystems/Perkin Elmer) and piperidine (Aldrich Chemical Co., St. Louis, Mo.), and used for synthesis reagents.

The Peptide Companion software (Peptides International, Louisville, Ky.) was used to predict the aggregation potential and difficulty level for synthesis for the zsig33-1 peptide. Synthesis was performed using single coupling programs, according to the manufacturer's specifications.

The peptide was cleaved from the solid phase following standard TFA cleavage procedure (according to Peptide Cleavage manual, Applied Biosystems/Perkin Elmer). Purification of the peptide was done by RP-HPLC using a C18, 10 µm semi-peparative column (Vydac, Hesperial, Calif.). Eluted fractions from the column were collected and analyzed for correct mass and purity by electrospray mass spectrometry. Two pools of the eluted material were collected. The mass spectrometry analysis results indicated that both pools contained the purified form of zsig33 with a mass of 1600 Daltons. This was the expected mass, so the pools were combined, frozen and lyophilized.

Example 5

Construction of Expression Vector Expressing Full-Length GHS-R

The entire GHS-R is isolated from a plasmid containing GHS-R cDNA by PCR using primers also containing BamHI and EcoRI sites. The reaction conditions are as follows: 95° C. for 1 min; 35 cycles at 95° C. for 1 min, 55° C. for 1 min, 72° C. for 2 min; followed by 72° C. at 10 min; then a 10° C. soak. The PCR product is run on a 1% low melting point agarose (Boerhinger Mannheim) and the approximately 1.05 kb GHS-R cDNA is isolated using Qiaquick™ gel extraction kit (Qiagen) as per manufacturer's instructions.

The purified GHS-R cDNA is digested with BamHI (Boerhinger Mannheim) and EcoRI (BRL) as per manufacturer's instructions. The entire digest is run on a 1% low melting point agarose (Boerhinger Mannheim) and the fragment is purified using Qiaquick gel extraction kit as per manufacturer's instructions. The resultant cleaved GHS-R is inserted into an expression vector as described below.

Recipient expression vector pZP-5N is digested with BamHI (Boerhinger Mannheim) and EcoRI (BRL) as per manufacturer's instructions, and gel purified as described above. This vector fragment is combined with the BamHI and EcoRI cleaved GHS-R fragment isolated above in a ligation reaction. The ligation is run using T4 Ligase (BRL), at 15° C. overnight. A sample of the ligation is electroporated in to DH10B electroMAX™ electrocompetent *E. coli* cells (25 g, 200Ω, 2.3V). Transformants are plated on LB+Ampicillin plates and single colonies screened by PCR to check for the GHS-R sequence new primers and using the PCR conditions as described above.

Confirmation of the GHS-R sequence is made by sequence analyses. The insert is approximately 1.1 kb, and is full-length.

Example 6

Construction of BaF3 Cells Expressing GHS-R

BaF3, an interleukin-3 (IL-3) dependent pre-lymphoid cell line derived from murine bone marrow (Palacios and Steinmetz, Cell 41: 727-734, 1985; Mathey-Prevot et al., Mol. Cell. Biol. 6: 4133-4135, 1986), is maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, pZP-5N/GHS-R cDNA (Example 5) is prepared and purified using a Qiagen Maxi Prep kit (Qiagen) as per manufacturer's instructions. BaF3 cells for electroporation are washed once in RPMI media and then resuspended in RPMI media at a cell density of $10^7$ cells/ml. One ml of resuspended BaF3 cells is mixed with 30 µg of the pZP-5N/GHS-R plasmid DNA and transferred to separate disposable electroporation chambers (GIBCO BRL). Following a 15 minute incubation at room temperature the cells are given two serial shocks (800 1Fad/300 V.; 1180 1Fad/300 V.) delivered by an electroporation apparatus (CELL-PORATOR™; GIBCO BRL). After a 5 minute recovery time, the electroporated cells are transferred to 50 ml of complete media and placed in an incubator for 15-24 hours (37° C., 5% $CO_2$). The cells are then spun down and resuspended in 50 ml of complete media containing Geneticin™ (Gibco) selection (500 µg/ml G418) in a T-162 flask to isolate the G418-resistant pool. Pools of the transfected BaF3 cells, hereinafter called BaF3/GHS-R cells, are assayed for zsig33 binding capability as described below.

Example 7

Screening for GHS-R Activity Using BaF3/GHS-R Cells Using an Alamar Blue Proliferation Assay BaF3/GHS-R cells are spun down and washed in mIL-3 free media 3 times to ensure the removal of the mIL-3 Cells are then counted in a hemacytometer, and plated in a 96-well format at 5000 cells per well in a volume of 100 µl per well using the mIL-3 free media.

Proliferation of the BaF3/GHS-R cells is assessed using media containing synthesized zsig33 which has been diluted with mIL-3 free media to 50%, 25%, 12.5%, 6.25%, 3.125%, 1.5%, 0.75% and 0.375% (of zsig33) concentrations. 100 µl of the diluted synthesized zsig33 is added to the BaF3/GHS-R cells. The total assay volume is 200 µl. Negative controls are run in parallel using mIL-3 free media only, without the addition of zsig33. The assay plates are incubated at 37° C., 5% $CO_2$ for 3 days at which time Alamar Blue (Accumed, Chicago, Ill.) is added at 20 µl/well. Alamar Blue gives a fluourometric readout based on number of live cells, and is thus a direct measurement of cell proliferation in comparison to a negative control. Plates are again incubated at 37° C., 5% $CO_2$ for 24 hours. Plates are read on the Fmax™ plate reader (Molecular Devices Sunnyvale, Calif.) using the SoftMax™ Pro program, at wavelengths 544 (Excitation) and 590 (Emmission).

A positive result is measured as approximately 4-fold over background when the BaF3 wild type cells do not proliferate at the same concentration. Additional variants, produced synthetically, or recombinantly, are also screened in this manner.

Similarly, antibodies to zsig33 or GHS-R may be tested in this manner for inhibition/antagonism of the zsig33 ligand.

Example 8 zsig33 Anti-Peptide Antibodies

Polyclonal anti-peptide antibodies were prepared by immunizing two female New Zealand white rabbits with the peptide, huzsig33-2 (SEQ ID NO:16). The peptide was synthesized using an Applied Biosystems Model 431A peptide synthesizer (Applied Biosystems, Inc., Foster City, Calif.) according to manufacturer's instructions. The peptides were then conjugated to the carrier protein maleimide-activated keyhole limpet hemocyanin (KLH) through cysteine residues (Pierce, Rockford, Ill.). The rabbits were each given an initial intraperitoneal (IP) injection of 200 mg of conjugated peptide in Complete Freund's Adjuvant (Pierce, Rockford, Ill.) followed by booster IP injections of 100 mg conjugated peptide in Incomplete Freund's Adjuvant every three weeks. Seven to ten days after the administration of the third booster injection, the animals were bled and the serum was collected. The rabbits were then boosted and bled every three weeks.

The zsig33 peptide-specific antibodies were affinity purified from the rabbit serum using an CNBr-SEPHAROSE 4B peptide column (Pharmacia LKB) that was prepared using 10 mg of the zsig33 peptide per gram CNBr-SEPHAROSE, followed by dialysis in PBS overnight. Peptide specific-zsig33 antibodies were characterized by an ELISA titer check using 1 mg/ml of the appropriate peptide as an antibody target.

Example 9

Binding Studies of zsig33 In Situ

Ten week old Balb C male mice were anesthetized via intramuscular injection and tested for binding of zsig33 peptides in vivo.

Two peptides were tested: the first peptide, zsig33-1, (See Example 4) consisted of residues 24 to 37 of SEQ ID NO:2, and the second peptide, zsig33-2, consisted of residues 24 to 41 of SEQ ID NO:2. A single glycine was used as a negative control. Additionally, a "scrambled" negative control consisting of residues the first peptide which had been rearranged (SEQ ID NO:15) was also tested. The peptides and controls were coupled to fluorescein isothiocyantate (FITC, Molecular Probes, Eugene, Oreg.) in the following manner: The peptides, glycine control and FITC were dissolved in 0.1 M sodium bicarbonate at pH 9.0 to a concentration of 2.0 mg/ml for the peptides and glycine control and 5 mg/ml for FITC, avoiding exposure of the FITC to strong light. The FITC/sodium bicarbonate solution was added to the peptides at a ratio of 1 mg FITC to 1 mg peptide or glycine control, and allowed to react in the dark at ambient room temperature for 1 hour. The FITC-conjugated peptides and glycine control were dialyzed in a 1 K dialysis membrane and 0.1 M sodium bicarbonate buffer at 4° C. The buffer was changed daily and unbound FITC in the post-dialyzed buffer was measured by HPLC. After six days, the buffer was changed to phosphate buffered saline (PBS) and dialyzed for two days followed by another change in PBS and dialyzed for another 2 days. Peptide- or glycine-bound FITC was determined by measuring the absorbance of the dialyzed FITC-bound material at 498 nm and dividing by the extinction coefficient of fluorescein, 0.083 μM. The molar ratio of fluorescein to peptide (mole FITC/mole peptide) was then determined.

The labeled peptides were administered via tail vein injections such that each mouse received 0.5 ml (0.5 mg) of labeled peptide which was allowed to circulate in the mice for 15 minutes following injection.

While under anesthesia the right atrium of each mouse was snipped to allow an exit path and 20 ml of PBS was injected into left ventricle and used to flush the circulatory system. The mice were then perfused with approximately 10 ml of formalin in neutral buffer (10% Neutral Buffered Formalin (NBF), Surgipath, Richmond, Ill.).

Tissues of liver, kidney, heart, lung, thymus, spleen, duodenum, ileum, jejunum colon and stomach were harvested by dissection, and fixed overnight in 10% NBF before processing for histological evaluation. Tissues were processed in the V.I.P. 2000 (Miles, Inc., Elkhart, Ind.) resulting in Paraffin® infiltration of the tissue. The tissue/Paraffin® blocks were sliced into 5 μm sections in a Jung Biocut (Leica, Nussloch, Germany), placed on glass slides, and incubated at 60° C. for one hour to aid in adhering the tissue to the slide. The Paraffin® was removed by washing the slides three times in 100% xylene for 5 minutes. The slides were then rehydrated by 2 washes in 100% ethanol for 3 minutes; followed by one wash in 95% ethanol. The slides were allowed to dry and then mounted with 5 to 10 μl of antifade medium which was prepared by adding nine parts glycerol containing 2% DABCO (1,4-diazobicyclo-(2,2,2,)-octane, Sigma, St. Louis, Mo.), dissolved at 55-70° C. to one part 0.2 M Tris/HCL, pH 7.5 DAPI (Sigma, St. Louis, Mo.) or propididum iodide (0.5 μg/ml). See also Kievits, T. et al., *Cytogenet Cell Cenet* 53:134-136 (1990) for antifade medium. Slides were covered with cover slips and immediately examined by fluorescent microscopy at 495 nm.

Results indicated the labeled zsig33 peptides, zsig33-1 and zsig33-2, showed increased fluorescence in duodenum, jejunum and in the collecting ducts and convoluted tubules of the kidney compared to the glycine and "scrambled" controls. Other tissues showed similar fluorescence compared to the negative controls.

Example 10

Effects of zsig33 on Gastrointestinal Contractility

Two male Sprague-Dawley rats, approximately 12 weeks old (Harlan, Indianapolis, Ind.) were anesthetized with urethane and their stomachs were exposed through a small abdominal incision. Two 2.4 mm transducing crystals (Sonometrics, Ontario, Canada) were placed on the antral portion of the stomach such that circular contractions could be monitored as a change in the distance between the two crystals. The crystals were attached with VETBOND TISSUE ADHESIVE (3M, St. Paul, Minn.).

10 ml of 1 mM acetylcholine was applied topically to the stomach between the two crystals, and resulted in a rapid, but transient increase in the distance between two crystals. 10 ml of norepinephrine (NE) at 1 mM caused a reduction in the distance between the two crystals. The amplitude of the NE-induced decrease was approximately 50% of the acetylcholine-induced increase in distance. Both responses were transient.

A negative control of 10 ml of phosphate buffer solution (PBS) applied topically between the crystals had no effect.

A 14 amino acid zsig33 peptide (zsig33-1, as shown in Example 4) was dissolved in PBS and 10 ml was applied topically for a final concentration of 1 mg, 10 mg or 100 mg. The zsig33 peptide at 1 mg induced a sustained, rhythmic increase and decrease in crystal distance. This effect appeared

Example 11

Effects of Zsig33 on Glucose Absorption

Eight female ob/ob mice, approximately 6 weeks old (Jackson Labs, Bar Harbor, Me.) were adapted to a 4 hour daily feeding schedule for two weeks. After two weeks on the feeding schedule, the mice were given 100 mg of a zsig33 peptide (zsig33-1, as shown in Example 4) in 100 ml sterile 0.1% BSA by oral gavage, immediately after their eating period (post-prandially). Thirty minutes later, the mice were challenged orally with a 0.5 ml volume of 25% glucose. Retroorbital bleeds were done to determine serum glucose levels. Blood was drawn prior to zsig33 dosing, prior to oral glucose challenge, and at 1, 2, 4, and 20 hours following the glucose challenge.

When zsig33 peptide was given orally at 100 mg, 30 minutes prior to an oral glucose challenge, an enhanced postprandial glucose absorption was seen.

Example 12

Effects of Zsig33 on Gastric Emptying

The effect of topically applied zsig33 peptide (amino acid 24 to 37 of SEQ ID NO: 2) on the transit of phenol red through the stomachs of fasted male Sprague-Dawley rats (Harlan, Indianapolis, Ind.) was evaluated. The rats (6 animals, 8 weeks old) were fasted 24 hrs prior to being anesthetized with urethane (0.5 ml/100 grams of 25% solution). After anesthetizing, the animals were orally gavaged with 1 ml of Phenol Red solution (50 mg/ml in 2% methylcellulose solution).

The stomach of each animal was exposed through a small abdominal incision and either 1 µg zsig33 peptide or a 14 amino acid control of a scrambled sequence peptide was applied topically to the stomach five minutes following the gavage. The amount of Phenol Red remaining in the stomach was determined by measuring optical density of the extracted stomach contents 30 minutes after the gavage.

The zsig33 peptide reduced the amount of Phenol Red remaining in the stomach by approximately 25% compared to a scrambled peptide, indicating that the zsig33 peptide enhanced gastric emptying in these rats.

Example 13

Effects of Zsig33 on Body Weight, Food Intake, and Glucose Clearance

Sixteen female ob/ob mice, 8 weeks old, (Jackson Labs, Bar Harbor, Me.) were adapted to a special 4 hour daily feeding schedule for two weeks. The were fed ad libitum from 7:30-11:30 am daily. After two weeks on the feeding schedule, the mice were divided into two groups of 8. One group was given 1.0 mg/mouse of zsig33-1 (14 amino acid peptide) and the other vehicle (a 14 amino acid scrambled sequence peptide) in 100 ml sterile 0.1% BSQA by oral gavage just prior to receiving food, and at the end of the 4 hour feeding period. The mice were injected twice daily for fourteen days, during which time food intake and body weight was measured daily. On day 14, immediately after the second oral gavage of the zsig33-1 peptide, the mice were challenged orally with an 0.5 ml volume of 25% glucose. Retro-orbital bleeds were done to determine serum glucose levels immediately prior to administration of the zsig33-1 peptide or vehicle (t=30 min.), and also at 0, 1, 2, and 4 hours following the glucose challenge.

Results indicated that when zsig33-1 given orally at 1 mg/mouse had no affect on daily body weight or food intake measurements, or on glucose clearance as determined on day 14.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. A method of purifying a peptide comprising;
   immobilizing cells expressing a receptor on a solid support, wherein the receptor comprises residues 41 to 326 of SEQ ID NO:5;
   contacting the immobilized cells with a solution containing a peptide, wherein the peptide comprises residues 24 to 37 of SEQ ID NO:2; and
   forming a peptide-receptor complex;
   whereby the peptide is purified.

2. The method of claim 1, wherein the receptor comprises residues 41 to 366 of SEQ ID NO:5.

3. The method of claim 1, wherein the peptide comprises residues 24 to 41 of SEQ ID NO:2.

4. The method according to claim 1, wherein the solid support is selected from the group consisting of:
   a) agarose;
   b) glass;
   c) cellulosic resins;
   d) silica-based resins;
   e) polystyrene; and
   f) cross-linked polyacrylamide.

5. The method according to claim 1, comprising the additional step of washing the peptide-receptor complex with buffer to remove unbound receptor.

6. The method according to claim 1, comprising the additional step of dissociating the peptide-receptor complex.

7. The method according to claim 1, comprising the additional step of recovering the purified receptor-expressing cells.

8. A method of purifying a peptide comprising;
   immobilizing cells expressing a receptor, wherein the receptor comprises residues 41 to 326 of SEQ ID NO:5;
   contacting the immobilized cells with a solution containing a peptide, wherein the peptide comprises residues 24 to 37 of SEQ ID NO:2;
   forming a peptide-receptor complex; and
   detecting the binding of the peptide to the receptor wherein the peptide is labelled;
   whereby the peptide is purified.

9. The method according to claim 8, wherein the label is selected from the group consisting of:
   a) a radiolabel;
   b) a photoaffinity label; and
   c) a fluorescent label.

10. The method according to claim 8, wherein the label is a radiolabel.

11. The method according to claim 8, wherein the label is a photoaffinity label.

12. The method according to claim 8, wherein the label is a fluorescent label.

13. The method of claim 8, wherein the receptor comprises residues 41 to 366 of SEQ ID NO:5.

14. The method of claim 8, wherein the peptide comprises residues 24 to 41 of SEQ ID NO:2.

15. The method according to claim 8, comprising the additional step of dissociating the peptide-receptor complex.

16. The method according to claim 8, comprising the additional step of recovering the purified receptor-expressing cells.

17. The method according to claim 4, wherein the solid support is selected from the group consisting of
   a). agarose;
   b). glass;
   c). cellulosic resins;
   d). silica-based resins;
   e). polystyrene; and
   f). cross-linked polyacrylamide.

* * * * *

UNITED STATES PATENT AND TRADEMARK OFFICE
CERTIFICATE OF CORRECTION

PATENT NO.       : 8,124,356 B2  
APPLICATION NO.  : 13/016537  
DATED            : February 28, 2012  
INVENTOR(S)      : Paul O. Sheppard et al.

Page 1 of 1

It is certified that error appears in the above-identified patent and that said Letters Patent is hereby corrected as shown below:

In the Claims:

Column 75  
Line 41, delete "complex;" and insert -- complex and eluting the bond peptide from the peptide-receptor complex; --; and  
Line 63, delete "receptor," and insert -- receptor onto a solid support, --.

Column 76  
Line 37, before "whereby" insert -- eluting the bound peptide from the peptide-receptor complex, --.

Signed and Sealed this  
Thirtieth Day of April, 2013

Teresa Stanek Rea  
*Acting Director of the United States Patent and Trademark Office*